US008501818B2

(12) United States Patent
Alonso et al.

(10) Patent No.: US 8,501,818 B2
(45) Date of Patent: *Aug. 6, 2013

(54) STABILIZED COMPOSITIONS OF ALKYLATING AGENTS AND METHODS OF USING SAME

(75) Inventors: Robert Alonso, Rye, NH (US); Martin Stogniew, Blue Bell, PA (US); Peter A. Crooks, Nicholasville, KY (US); Mark A. Pimley, Westchester, PA (US); David R. Worthen, Wakefield, RI (US)

(73) Assignee: Ceptaris Therapeutics, Inc., Malvern, PA (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/687,605

(22) Filed: Jan. 14, 2010

(65) Prior Publication Data

US 2010/0152300 A1 Jun. 17, 2010

Related U.S. Application Data

(63) Continuation-in-part of application No. 11/369,305, filed on Mar. 7, 2006, now Pat. No. 7,872,050, and a continuation-in-part of application No. 12/401,812, filed on Mar. 11, 2009.

(60) Provisional application No. 60/661,356, filed on Mar. 14, 2005, provisional application No. 60/751,128, filed on Dec. 16, 2005, provisional application No. 61/039,840, filed on Mar. 27, 2008.

(51) Int. Cl.
*A01N 33/02* (2006.01)
*A61K 31/13* (2006.01)

(52) U.S. Cl.
USPC .......................................... 514/672; 424/400

(58) Field of Classification Search
USPC .......................................... 514/672; 424/400
See application file for complete search history.

(56) References Cited

U.S. PATENT DOCUMENTS

| | | |
|---|---|---|
| 3,767,792 A | 10/1973 | Cook et al. |
| 3,904,766 A | 9/1975 | Van Scott et al. |
| 4,083,692 A | 4/1978 | Epstein et al. |
| 4,206,222 A | 6/1980 | Valetas |
| 4,725,438 A | 2/1988 | Leazer |
| 4,853,388 A | 8/1989 | Pearlman |
| 4,863,910 A | 9/1989 | Takayanagi |
| 4,888,344 A | 12/1989 | Sunagawa et al. |
| 4,888,354 A | 12/1989 | Chang et al. |
| 4,949,641 A | 8/1990 | Sayles |
| 5,051,363 A | 9/1991 | Ritter et al. |
| 5,229,422 A | 7/1993 | Takahashi et al. |
| 5,326,790 A | 7/1994 | Thornfeldt |
| 5,616,332 A | 4/1997 | Herstein |
| 5,719,197 A | 2/1998 | Kanios et al. |
| 5,744,460 A | 4/1998 | Muller et al. |
| 5,820,872 A | 10/1998 | Edelson et al. |
| 5,824,650 A | 10/1998 | De Lacharriere et al. |
| 5,948,437 A | 9/1999 | Parikh et al. |
| 5,972,892 A | 10/1999 | De Lacharriere et al. |
| 6,005,002 A | 12/1999 | Springer et al. |
| 6,017,902 A | 1/2000 | Glass |
| 6,124,108 A | 9/2000 | Ray |
| 6,255,502 B1 | 7/2001 | Penkler et al. |
| 6,329,148 B1 | 12/2001 | Rosen et al. |
| 6,472,435 B1 | 10/2002 | Boyle |
| 6,692,742 B1 | 2/2004 | Nakamura et al. |
| 6,753,155 B1 | 6/2004 | Ray |
| 7,323,171 B2 | 1/2008 | Wallner et al. |
| 7,470,433 B2 | 12/2008 | Carrara et al. |
| 2001/0049349 A1* | 12/2001 | Chinery et al. ................... 514/1 |
| 2002/0142028 A1* | 10/2002 | Elliesen et al. ............... 424/449 |
| 2002/0146692 A1 | 10/2002 | Yamazaki et al. |
| 2003/0083321 A1 | 5/2003 | Lerner et al. |
| 2003/0087961 A1 | 5/2003 | Ko et al. |
| 2003/0215471 A1 | 11/2003 | Wilmott et al. |
| 2005/0039228 A1 | 2/2005 | Ding et al. |
| 2006/0079492 A1 | 4/2006 | Ahlem et al. |
| 2006/0205694 A1 | 9/2006 | Alonso et al. |
| 2006/0281720 A1 | 12/2006 | Loria |
| 2007/0287719 A1 | 12/2007 | Boyden et al. |
| 2008/0194699 A1 | 8/2008 | Alonso et al. |
| 2009/0247645 A1 | 10/2009 | Alonso et al. |
| 2009/0312290 A1 | 12/2009 | Panasci et al. |
| 2010/0029783 A9 | 2/2010 | Alonso et al. |
| 2010/0041767 A1 | 2/2010 | Alonso et al. |
| 2011/0039943 A1 | 2/2011 | Alonso et al. |
| 2011/0065803 A1 | 3/2011 | Alonso et al. |

FOREIGN PATENT DOCUMENTS

| | | |
|---|---|---|
| EP | 0317281 A2 | 5/1989 |
| EP | 0317281 A3 | 8/1989 |
| WO | WO 87/04154 A1 | 7/1987 |
| WO | WO 99/42578 A2 | 8/1999 |

(Continued)

OTHER PUBLICATIONS

Reepmeyer, J.C. "Analysis of the nitrogen mustard mechlorethamine in topical pharmaceutical preparations by high-performance liquid chromatography" Journal of Chrmatography A, 2005, vol. 1085, pp. 262-269.*

Arrazola et al., "Treatment of alopecia areata with topical nitrogen mustard," Int J Dermatol 24(9):608-10, 1985.

Bernardo et al., "Topical nitrogen mustard in the treatment of alopecia areata: a bilateral comparison study," J Am Acad Dermatol 49(2):291-4, 2003.

Connors et al., "Mechlorethamine," Chemical Stability of Pharmaceuticals. A Handbook for Pharmacists, Second Edition (John Wiley & Sons, Inc.) pp. 529-533, 1986.

Tang et al., "Topical mechlorethamine restores autoimmune-arrested follicular activity in mice with an alopecia areata-like disease by targeting infiltrated lymphocytes," J Invest Dermatol 120(3):400-6, 2003.

Final office action mailed on Jul. 6, 2010 in connection with U.S. Appl. No. 11/908,531.

(Continued)

*Primary Examiner* — Kendra D Carter
(74) *Attorney, Agent, or Firm* — Wilson Sonsini Goodrich & Rosati

(57) ABSTRACT

Provided are stable compositions comprising alkylating agents, including nitrogen mustards, that are suitable for topical use, and methods for treating skin disorders comprising topically administering the compositions.

24 Claims, 11 Drawing Sheets

FOREIGN PATENT DOCUMENTS

| WO | WO 99/42578 A3 | 12/1999 |
|---|---|---|
| WO | WO 03/037380 A1 | 8/2003 |
| WO | WO 2004/050057 A2 | 6/2004 |
| WO | WO 2004/050057 A3 | 9/2004 |
| WO | WO 2005007129 A2 * | 1/2005 |
| WO | WO 2005/007129 A3 | 8/2005 |
| WO | WO 2006/099385 | 9/2006 |
| WO | WO 2009/120493 | 10/2009 |

OTHER PUBLICATIONS

Khan et al., "Hepatocyte toxicity of mechlorethamine and other alkylating anticancer drugs. Role of lipid peroxidation," Biochem Pharmacol 43(9):1963-7 (1992).
Wu et al., "Elucidation of the chemical structures of natural antioxidants isolated from rosemary," JAOCS 59(8):339-345 (1982).
Non-final office action mailed Feb. 19, 2010 in U.S. Appl. No. 11/908,531.
PCT/US2009/036737 International Search Report mailed Jan. 11, 2010.
Non-final office action mailed on Jan. 27, 2011 in connection with U.S. Appl. No. 11/908,531.
Mechlorethamine (Topical), Drugs.com, Drug information online www.drugs.com/mmx/mechlorethamine-hydrochloride.html, Jun. 14, 2010.
Chabner et al., "Antineoplastic agents," Goodman & Gilman's The Pharmacological Basis of Therapeutics, Tenth Edition, Chapter 52, pp. 1389-1397, 2001.
Bell, "The effect of the solvent on protolytic equilibria," The Proton in Chemistry, Second Edition (Cornell University Press) pp. 44-55, 1959.
Non-final office action mailed Jun. 10, 2010 in connection with U.S. Appl. No. 12/549,258.
European search report and opinion dated Mar. 31, 2008 for EP Application No. 06738150.9.
Bonina et al., Vehicle effects on in vitro skin permeation of and stratum corneum affinity for model drugs caffeine and testosterone, Int J Pharmaceutics, 100:41-47, 1993.
Cummings et al., The long term stability of mechlorethamine hydrochloride (nitrogen mustard) ointment measured by HPLC, J Pharm Pharmacol 45:6-9, 1993.
Foulec et al., Evaluation of a 1-h exposure time to mechlorethamine in patients undergoing topical treatment, Brit J Derm 147:926-930, 2002.
Kim et al., Topical Nitrogen Mustard in the Management of Mycosis Fungoides, Arch Dermatol 139:165-173, 2003.
Kravitz et al., Topical nitrogen mustard induced carcinogenesis, Acta Derm Venereol, 1978 (abstract).
Price, Ointment-based mechlorethamine treatment for mycosis fungoides, Cancer 52:2214-2219, 1983.
Tang et al., Topical mechlorethamine restores autoimmune-arrested follicular activity in mice with an alopecia areata-like disease by targeting infiltrated lymphocytes, J Inv Derm, 120(3):400-406, 2003.
Taylor et al., Mechlorethamine hydrochloride solutions and ointment prolonged stability and biological activity, Arch Dermatol, 116(7):783-5, 1980.
Wormser et al., Noninvasive procedure for in situ determination of skin surface aspartic proteinase activity in animals; implications for human skin, Arch Dermatol Res, 289: 686-691, 1997.
Ritschel, et al., Stability of the nitrogen mustard mechlorethamine in novel formulations for dermatological use, Int'l J. Pharm., 362: 67-73, 2008.
Lessin et al., Testing efficacy and safety of topical nitrogen mustard in mycosis fungoides, submitted to 21$^{st}$ World Congress of Dermatology in Buenos Aires, Oct. 1-5, 2007.
Lessin, Nitrogen mustard (NM) ointment formulation containing propylene glycol (PG) is active in treating mycosis fungoides (MF), J Inv Dermatol, 2007 (abstract).
Non-final office action mailed Dec. 24, 2009 in U.S. Appl. No. 11/369,305.
PCT/US2006/009060 International Search Report mailed Jan. 28, 2008.
Alonso et al., U.S. Appl. No. 12/549,258, filed Aug. 27, 2009, entitled "Stabilized compositions of volatile alkylating agents and methods of using thereof," currently pending, and claims as amended on Oct. 30, 2009.
U.S. Appl. No. 13/300,021, filed Nov. 18, 2011, Alonso et al.
Morissette, et al. High-throughput crystallization: polymorphs, salts, co-crystals and solvates of pharmaceutical solids. Advanced Drug Delivery Reviews. 2004; 56:275-300.
Ash, et al. Handbook of preservatives. Synapse Information Resources, Inc. 2004, pp. 292, 294 and 379.
International search report and written opinion dated Sep. 18, 2012 for PCT/US2012/046155.
Notice of allowance dated Jan. 8, 2013 for U.S. Appl. No. 11/908,531.
Notice of allowance dated Oct. 5, 2012 for U.S. Appl. No. 11/908,531.
Office action dated Mar. 8, 2012 for U.S. Appl. No. 11/908,531.
Office action dated May 24, 2012 for U.S. Appl. No. 12/948,593.
Office action dated Aug. 16, 2012 for U.S. Appl. No. 12/401,812.
Office action dated Aug. 31, 2011 for U.S. Appl. No. 11/908,531.
Office action dated Oct. 9, 2012 for U.S. Appl. No. 12/890,183.
Office action dated Nov. 9, 2011 for U.S. Appl. No. 12/948,593.
Office action dated Dec. 21, 2011 for U.S. Appl. No. 12/401,812.
Quatrebarbes, et al. Treatment of early-stage mycosis fungoides with twice-weekly applications of mechlorethamine and topical corticosteroids: a prospective study. Arch Dermatol. Sep. 2005;141(9):1117-20.
Reepmeyer, C. Analysis of the nitrogen mustard mechlorethamine in topical pharmaceutical preparations by high-performance liquid chromatography. J Chromatogr A. Sep. 2, 2005;1085(2):262-9.
Novoembichin compound summary. PubMed. Http://pubchem.ncbi.nlm.nih.gov/summary/summary.cgi?cid=121547. Obtained Aug. 8, 2012.

* cited by examiner

STABILIZED COMPOSITIONS OF ALKYLATING AGENTS AND METHODS OF USING SAME

CROSS-REFERENCE TO RELATED APPLICATIONS

This application is a continuation-in-part of U.S. application Ser. No. 11/369,305, filed on Mar. 7, 2006, now U.S. Pat. No. 7,872,050, which claims the benefit of priority to U.S. provisional application Ser. Nos. 60/661,356, filed on Mar. 14, 2005 and 60/751,128, filed on Dec. 16, 2005, the contents of each of which are herein incorporated by reference. This application is also a continuation-in-part of U.S. application Ser. No. 12/401,812, filed on Mar. 11, 2009, which claims the benefit of priority to U.S. provisional application Ser. No. 61/039,840, filed on Mar. 27, 2008, the contents of each of which are herein incorporated by reference.

FIELD OF THE INVENTION

The invention encompasses stable compositions comprising alkylating agents, including nitrogen mustards, that are suitable for topical use, and methods for treating skin disorders comprising topically administering the compositions.

BACKGROUND OF THE INVENTION

Alkylating agents, such as nitrogen mustards, have been used in the pharmaceutical industry as anti-cancer drugs. For example, nitrogen mustards have been used to treat cutaneous T-cell lymphoma (CTCL), including mycosis fungoides (MF).

CTCL is a cancer of the white blood cells that primarily affects the skin and only secondarily affects other sites. The disease involves the uncontrolled proliferation of T-lymphocytes known as T-helper (CD4+) cells of the immune system. The proliferation of T-helper cells results in the penetration, or infiltration, of these abnormal cells into the epidermal layer of the skin. The skin reacts with slightly scaling lesions that itch, although the sites of greatest infiltration do not necessarily correspond to the sites of the lesions. The lesions are most often located on the trunk, but can be present on any part of the body. In the most common course of the disease, the patchy lesions progress to palpable plaques that are deeper red and have more defined edges. As the disease worsens, skin tumors develop that are often mushroom-shaped, hence the name mycosis fungoides. Finally, the cancer progresses to extracutanous involvement, often in the lymph nodes or the viscera.

CTCL is a rare disease, with an annual incidence of about 0.29 cases per 100,000 persons in the United States. It is about half as common in Eastern Europe. However, this discrepancy may be attributed to a differing physician awareness of the disease rather than a true difference in occurrence. In the United States, there are about 500-600 new cases a year and about 100-200 deaths. CTCL is usually seen in older adults; the median age at diagnosis is 55-60 years. It strikes twice as many men as women. The average life expectancy at diagnosis is 7-10 years, even without treatment.

Alkylating agents, such as nitrogen mustards, are believed to have anti-cancer activity by acting on the nucleic acids of DNA and RNA. Alkylating agents have four main actions on nucleic acids. First, the agents may cause crosslinking of DNA strands which interferes with DNA and RNA synthesis. This is thought to be the most important reason for the cytotoxic effect of alkylating agents. Secondly, the agents may alter the "side chain groups" of the nucleotide base ring which would lead to abnormal base pairing and point mutations in the synthesized DNA and RNA chains. Thirdly, the alkylating agents may split the base ring from the nucleotide which again interrupts proper DNA and RNA synthesis. Finally, the alkylating agents may break the ring structure of a nucleotide base which would prevent base pairing during DNA and RNA synthesis.

Nitrogen mustards are believed to act as anti-cancer agents by impairing natural DNA strand replication of cancer cells. In natural DNA strand replication, a DNA strand having deoxyribonucleosides, wherein each deoxyribonucleoside may include a base adenine (A), thymine (T), cytosine (C) and guanine (G), replicates by linking each deoxyribonucleoside on the strand with another deoxyribonucleoside, wherein typical linking occurs between adenine (A) and thymine (T), forming an A-T linkage, and between cytosine (C) and guanine (G), forming a C-G linkage, between the original DNA strand and its replicated DNA strand. Nitrogen mustards are believed to allow unnatural base-base linkages such as a guanine (G) base linking to another guanine (G) base if the particular nitrogen mustard is a bifunctional alkylator. As used herein, unless otherwise defined, a bifunctional alkylator is a nitrogen mustard that has at least two 2-chloroethyl side chains, for example, bis-(2-chloroethyl)methyl amine.

Nitrogen mustards may allow unnatural base-base linkages in DNA, for example, by the mechanism depicted in Reactions 1 to 4 below.

First, a nitrogen mustard, such as bis-(2-chloroethyl)methylamine (I) undergoes an intramolecular cyclization, resulting in formation of a highly reactive ethyleniminium intermediate (i.e., a aziridinium cation) (II) according to the following Reaction 1.

Reaction 1:

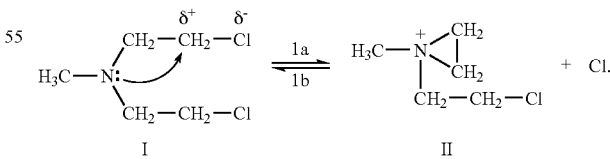

In the bis-(2-chloroethyl)methylamine (I), a carbon atom bonded to chlorine may initially have a partial positive charge, δ+, and a chlorine atom may initially have a partial negative charge, δ−. In Reaction 1, an unshared pair of electrons of nitrogen may form a covalent bond to the carbon having δ+, releasing the chlorine atom as chloride, and forming the ethyleniminium intermediate (II). A concentration of the ethyleniminium intermediate (II) may be in equilibrium with a concentration of the bis-(2-chloroethyl)methylamine (I) wherein the equilibrium constant $K_{eq(1a,1b)}$ may be represented by a ratio of a rate $_{k1a}$, of the forward reaction 1a, to a rate $_{k1b}$, of the reverse reaction 1b.

Second, the ethyleniminium intermediate (II) formed in Reaction 1 undergoes nucleophilic attack by an electron donor (i.e., a nucleophile, such as the guanine (III) of DNA), whereby the nucleophile is alkylated to form alkylated deoxyribonucleoside (IV) according to the following Reaction 2.

Reaction 2:

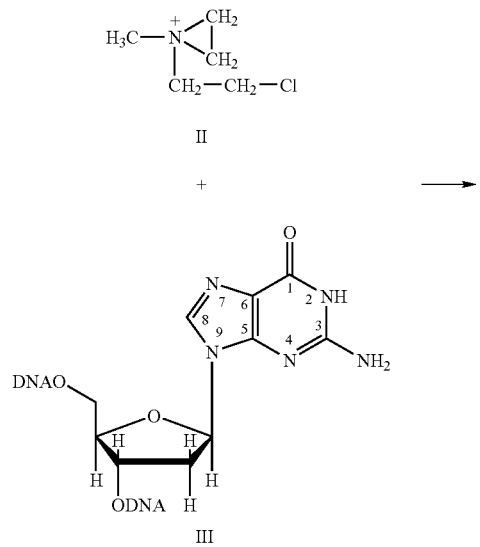

Reaction with the nucleophile guanine (III) at the position N-7 of the guanine occurs to the greatest extent. Other sites on guanine, and other DNA bases, such as adenine, cytosine, and thymine, and phosphate oxygens can also be alkyated.

Third, the alkylchloroethyl side chain of the alkylated deoxyribonucleoside (IV) formed in Reaction 2 undergoes intramolecular cyclization, resulting in formation of deoxyribonuceloside having a highly reactive aziridinium ring (V) according to the following Reaction 3.

Reaction 3:

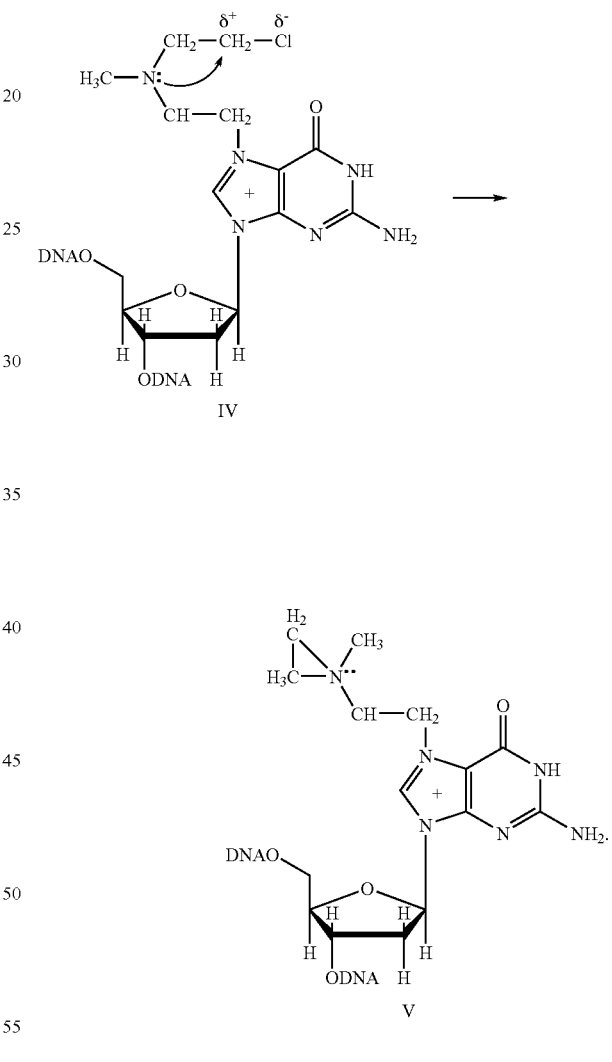

Finally, another guanine (III) of DNA reacts with the deoxyribonucleoside having a highly reactive aziridinium ring (V) formed in Reaction 3 to form an unnatural guanine-guanine link between two strands of DNA, as depicted in Structure (VI), according to the following Reaction 4.

Reaction 4:

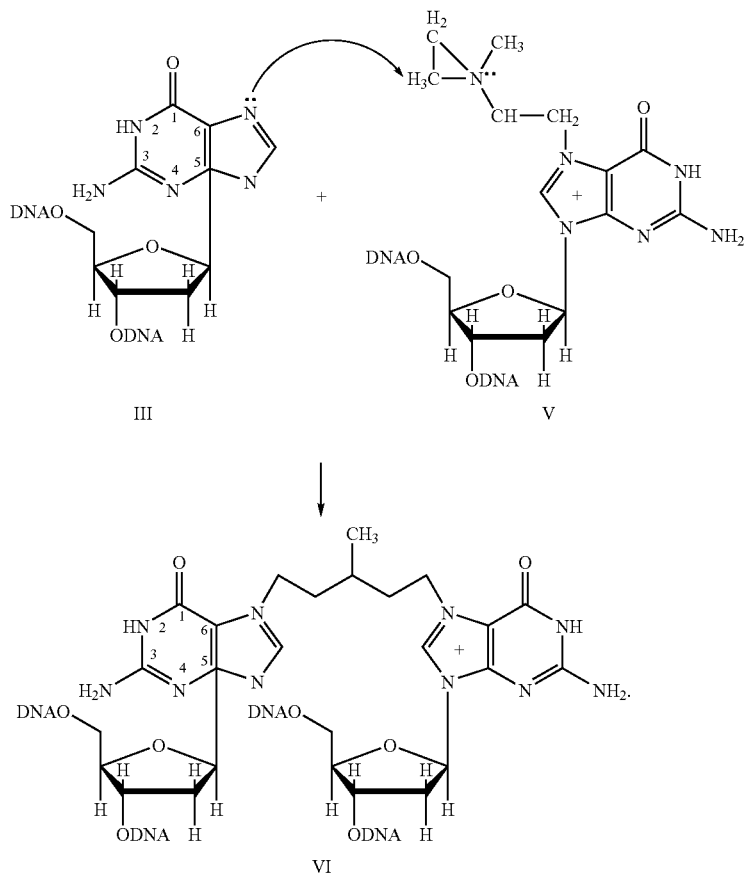

However, only the species which have the potential to form DNA cross-links, i.e. bifunctional species (I and II, Reactions 1-2) are believed to be the active forms of the nitrogen mustard alkylating agents;

The electrophilicity of alkylating agents, such as nitrogen mustards, causes them to be subject to decomposition in the presence of natural nucleophiles in the environment, such as water. In this work HPLC has been employed to determine the degradation products of mechlorethamine in ointment. The degradation (hydrolysis) of mechlorethamine is well characterized giving rise to N-methyl ethanolamine. Alternatively, the drug can degrade by reacting with a wide variety of nucleophiles to form covalent adducts.

Thus, there is a need in the art for stable compositions of alkylating agents, such as nitrogen mustards, that are suitable for topical use.

SUMMARY OF THE INVENTION

In one embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein at least about 90% of the bis-(2-chloroethyl)methylamine or pharmaceutically acceptable salt or solvate thereof is present in the composition after storage for at least about 3 months at a temperature of about −20° C. or higher.

In another embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein at least about 90% of the bis-(2-chloroethyl)methylamine or pharmaceutically acceptable salt or solvate thereof is present in the composition after storage for at least about 3 months at a temperature of about 2° C. or higher.

In another embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein at least about 90% of the bis-(2-chloroethyl)methylamine or pharmaceutically acceptable salt or solvate thereof is present in the composition after storage for at least about 1 month at a temperature of about 15° C. to about 30° C.

In another embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein the composition contains less than about 10% by weight of nitrogen mustard degradation product after storage for at least about 3 months at a temperature of about −20° C. or higher.

In another embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein the composition contains less than about 10% by weight of nitrogen mustard degradation product after storage for at least about 3 months at a temperature of about 2° C. or higher.

In another embodiment, the invention encompasses topical compositions comprising: (a) an effective amount of bis-(2-chloroethyl)methylamine or a pharmaceutically acceptable salt or solvate thereof; and (b) a pharmaceutically acceptable excipient, wherein the composition contains less than about 10% by weight of nitrogen mustard degradation product after storage for at least about 1 month at a temperature of about 15° C. to about 30° C.

In another embodiment, the invention encompasses topical compositions comprising: (a) an effective amount of bis-(2-chloroethyl)methylamine or a pharmaceutically acceptable salt or solvate thereof; and (b) a nitrogen mustard degradation product of the following Structure (DP-B) or (DP-D)

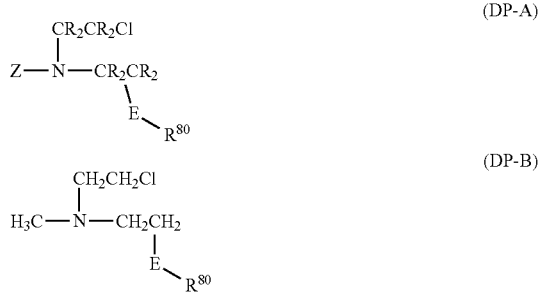

wherein:
each E is independently —O—, —NH—, —S—; —OC(O)CH(CH₃)OC(O)CH(CH₃)—; —OCH(CH₃)C(O)OCH(CH₃)—; or —O(CH₂)₂O(CH₂)₂O—; and
each $R^{80}$ is independently a linear or branched alkyl group having 1-12 carbon atoms, —COOH, or —OH.

DETAILED DESCRIPTION OF THE INVENTION

Figure 1:
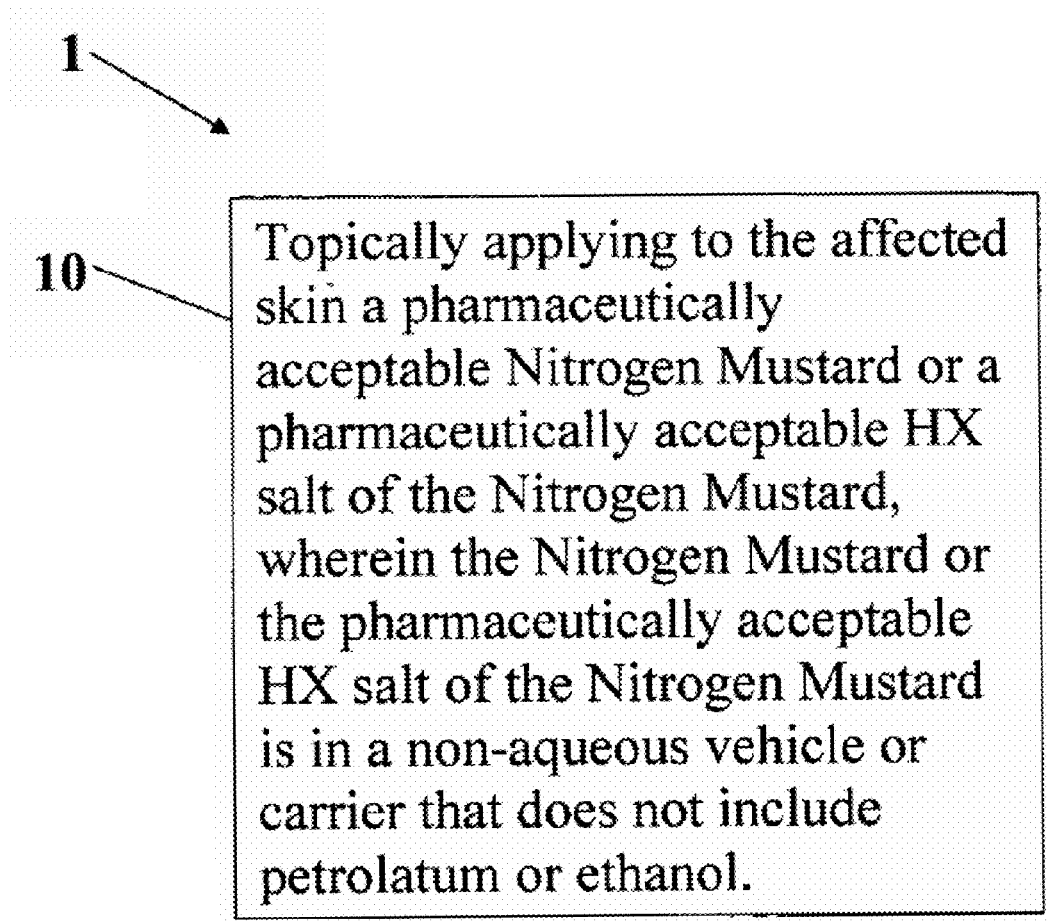
FIG. 1 illustrates a method for the use of compositions having stabilized alkylating agents for treating skin disease, in accordance with embodiments of the present invention.

The invention meets a need in the art by providing stable compositions of alkylating agents, such as nitrogen mustards, that are suitable for topical use, and methods of treatment therewith.

Not to be limited by theory, it is believed that nitrogen mustards are highly unstable and have an extremely short duration of action of in the presence of water because water decomposes the highly reactive ethyleniminium intermediate (aziridinium cation), represented by the structure (II) in Reaction 1, supra, replacing one or both chlorine atoms on the 2-chloroethyl side chains of the nitrogen mustard with an OH group.

I. DEFINITIONS

As used herein, unless otherwise defined, the term "stable," when referring to a composition of an alkylating agent, means that at least about 80% of the alkylating agent is present in the composition (in other words less than about 20% of the alkylating agent has degraded) after storage. Alternatively, the term "stable" means that the composition contains less than about 20% by weight of degradation product of the alkylating agent after storage.

As used herein, unless otherwise defined, the term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance, and bioavailability.

As used herein, unless otherwise defined, a "nitrogen mustard prodrug" is a compound that can be metabolized in vivo (i.e., can undergo chemical conversion my metabolic processes) to generate the nitrogen mustard.

As used herein, unless otherwise defined, "topical administration" means applying a drug to a localized area of the body or to the surface of a body part.

As used herein, unless otherwise defined, the term "effective amount" when referring to an alkylating agent means an amount of alkylating agent that is effective to treat a skin disorder.

As used herein, unless otherwise defined, the term "ameliorate" when referring to skin irritation means to lessen pain and reduce skin irritation.

As used herein, unless otherwise defined, the term "room temperature" means a temperature within the range of 15° C. to 30° C.

As used herein, unless otherwise defined, the term "degradation product," when referring to an alkylating agent, means a compound that can be formed by the degradation of the alkylating agent, for example, by reaction of the alkylating agent with a nucleophile to displace one or more of the functional groups of the alkylating agent.

As used herein, unless otherwise defined, the term "nitrogen mustard degradation product," means a compound that can be formed by the degradation of a nitrogen mustard, for example, by reaction of the nitrogen mustard with a nucleophile to displace one or more of the terminal chlorides of the nitrogen mustard.

II. COMPOSITIONS OF ALKYLATING AGENTS

In one embodiment, the invention encompasses a stable composition comprising an alkylating agent or a pharmaceutically acceptable salt or solvate thereof, and at least one pharmaceutically acceptable excipient.

In one embodiment, the composition is in the form of a paste, a dispersion, a suspension, a solution, a gel, a cream, or an ointment. In another embodiment, the composition is in the form of a dispersion. In another embodiment, the dispersion is a coarse dispersion, a colloidal dispersion, or a molecular dispersion.

Suitable alkylating agents include a nitrogen mustard, a sulfur mustard, a Lewisite, an alkyl sulfonate, an ethyleneimine, a nitrosourea, a triazene, an imidazotetrazine, mechlorethamine, chlorambucil, cyclophosphamide, 4-hydroxycyclophosphamide, aldophosphamide, ifosfamide, melphalan, bis-(2-chloroethyl)ethylamine, tris-(2-chloroethyl)ethylamine, carmustine, fotemustine, lomustine, streptozocin, busulfan, dacarbazine, procarbazine, temozolomide, treosulfan, uramustine, hexamethylmelamine, thiotepa (N,N',N''-triethylenethiophosphoramide), tepa (N,N',N''-triethylenephosphoramide), and pharmaceutically acceptable salts, solvates, and prodrugs thereof. In one embodiment, the alkylating agent is present in an amount of about 0.001% to about 50% w/w of the composition. In another embodiment, the alkylating agent is present in an amount of about 0.01% to about 0.04% w/w of the composition.

In one embodiment, the alkylating agent is a nitrogen mustard. In one embodiment, the nitrogen mustard is a compound of the following Structure (VII), (VIII), (IX), (X), (XII), (XIII), (XIV), (XV), (XVI), (XVII), (XVIII), or (XIX):

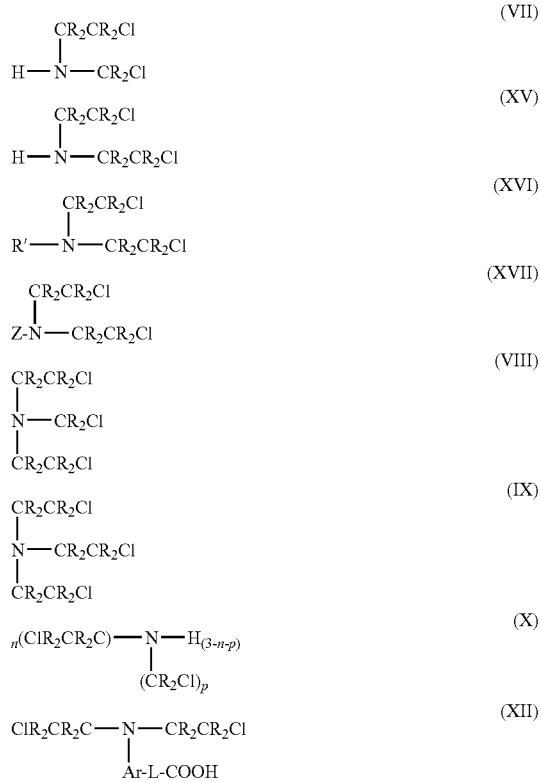

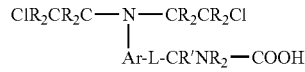

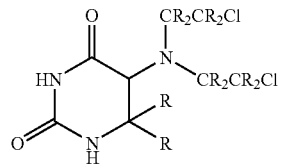

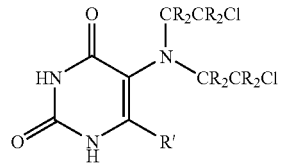

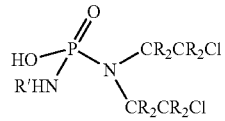

wherein:
each R and R' is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein any two R in the same molecule are optionally linked to form a three- to eight-membered cyclic group;

Z is a linear alkyl group having 1-6 carbon atoms;

each L is independently a linking group selected from the group consisting of linear or branched alkylene having 1 to 7 carbon atoms, cycloalkylene having 3 to 17 carbon atoms, alkylcycloalkylene having 4 to 20 carbon atoms, a cycloalkylalkylene having 4 to 20 carbon atoms, an arylene, having 4 to 30 carbon atoms, an alkylarylene, having 4 to 30 carbon atoms, an arylalkylene, having 4 to 30 carbon atoms, and combinations thereof;

each Ar is independently a bifunctional aromatic linking group wherein each Ar is selected from the group consisting of arylene, substituted arylene and heteroarylene;

n is 1, 2, or 3;

p is 0, 1, or 2; and $n+p \leq 3$.

Hereinafter, Structures (VII), (VIII), (IX), (X), (XII), (XIII), (XIV), (XV), (XVI), (XVII), (XVIII), and (XIX) may represent all racemic forms and stereoisomers wherein said compounds may be capable of optical activity.

In one embodiment, each R in Structure (VII), (VIII), (IX), (X), (XII), (XIII), (XIV), (XV), (XVI), (XVII), (XVIII) or (XIX) is hydrogen.

In one embodiment, the nitrogen mustard is a nitrogen mustard of Structure (XVII). In another embodiment, the nitrogen mustard is a nitrogen mustard of Structure (XVII), wherein the Z in structure (XVII) is methyl or ethyl. In another embodiment, the nitrogen mustard is a nitrogen mustard of Structure (XVII), wherein each R in structure (XVII) is independently a linear alkyl group having 1-6 carbon atoms. In another embodiment, the nitrogen mustard is a nitrogen mustard of Structure (XVII), wherein the Z in structure (XVII) is methyl or ethyl and each R in structure (XVII) is independently a hydrogen or linear alkyl group having 1-6 carbon atoms.

In another embodiment, the nitrogen mustard of structure (XVII) is bis-(2-chloroethyl)ethylamine or bis-(2-chloroethyl)methylamine (also known as mechlorethamine).

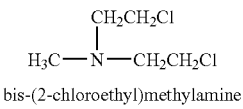

bis-(2-chloroethyl)methylamine

In one embodiment, the nitrogen mustard is a nitrogen mustard of Structure (IX). In another embodiment, the nitrogen mustard of Structure (IX) is tris-(2-chloroethyl)amine.

In one embodiment, the nitrogen mustard is a nitrogen mustard of Structure (XII). In another embodiment, the nitrogen mustard of structure (XII) is chlorambucil of Structure (XIIA):

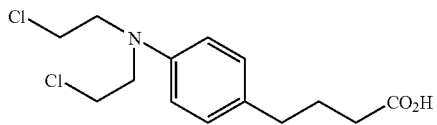

Structure (XII) may be cell cycle-phase nonspecific, although it also may be cytotoxic to nonproliferating cells. Activity may occur as a result of formation of an unstable ethylenimmonium ion, which alkylates or binds with many intracellular molecular structures, including nucleic acids. Its cytotoxic action may be primarily due to cross-linking of strands of DNA, which inhibits nucleic acid synthesis.

In one embodiment, the nitrogen mustard is a nitrogen mustard of Structure (XIII) In another embodiment, the nitrogen mustard of structure (XIII) is melphalan (also known as 4-bis(2-chloroethyl)amino-L-phenylalanine) of Structure (XIIIA):

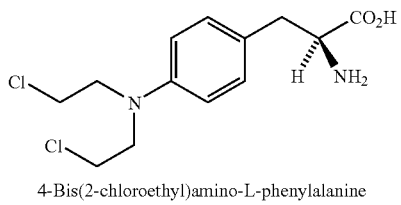

4-Bis(2-chloroethyl)amino-L-phenylalanine

Like the nitrogen mustards of Structure (XII), nitrogen mustards of Structure (XIII) may be cell cycle-phase nonspecific, although they also may be cytotoxic to nonproliferating cells.

In one embodiment, the nitrogen mustard is a nitrogen mustard of Structure (XVIII). In another embodiment, the nitrogen mustard of structure (XVIII) is uracil mustard of Structure (XVIIIA):

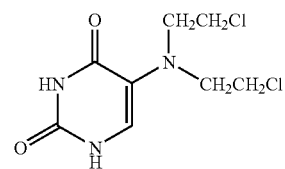

In one embodiment, the nitrogen mustard, pharmaceutically acceptable salt of the nitrogen mustard, or prodrug of the nitrogen mustard is present in an amount of about 0.0001% to about 10% by weight of the composition. In another embodiment, the nitrogen mustard, pharmaceutically acceptable salt of the nitrogen mustard, or prodrug of the nitrogen mustard is present in an amount of about 0.001% to about 2.0% by weight of the composition. In another embodiment, the nitrogen mustard, pharmaceutically acceptable salt of the nitrogen mustard, or prodrug of the nitrogen mustard is present in an amount of 0.01% to about 0.04% by weight of the composition. In another embodiment, the nitrogen mustard, pharmaceutically acceptable salt of the nitrogen mustard, or prodrug of the nitrogen mustard is present in an amount of 0.015% to about 0.04% by weight of the composition. In another embodiment, the nitrogen mustard, pharmaceutically acceptable salt of the nitrogen mustard, or prodrug of the nitrogen mustard is present in an amount of 0.015% to about 0.03% by weight of the composition.

In another embodiment, the nitrogen mustard is in the form of a pharmaceutically acceptable salt. Suitable pharmaceutically acceptable salts of nitrogen mustard include HX salts of the following Structures (VIIa), (VIIIa), (IXa), (Xa), (XIIa), (XIIIa), (XIVa), (XVa), (XVIa), (XVIIa), (XVIIIa), and (XIXa):

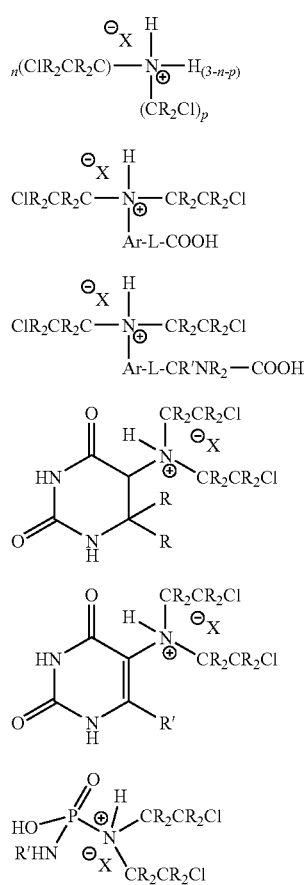

addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Illustrative base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

In some embodiments of the invention, use of the pharmaceutically acceptable HX salt of the nitrogen mustard, for example of structure (XXa, infra), may preserve the effective alkylating activity by reducing its volatility compared to that of the free base form of the nitrogen mustard, since pharmaceutically acceptable HX salts of nitrogen mustards generally have lower vapor pressures than their corresponding free base forms.

Reaction 5 illustrates competing equilibrium reactions, 1a and 1b and 5a and 5b. The reaction represented by arrow 5c, infra, illustrates the conversion of a free base nitrogen mustard to a pharmaceutically acceptable HX salt by reaction of the nitrogen mustard with HX.

Reaction 5:

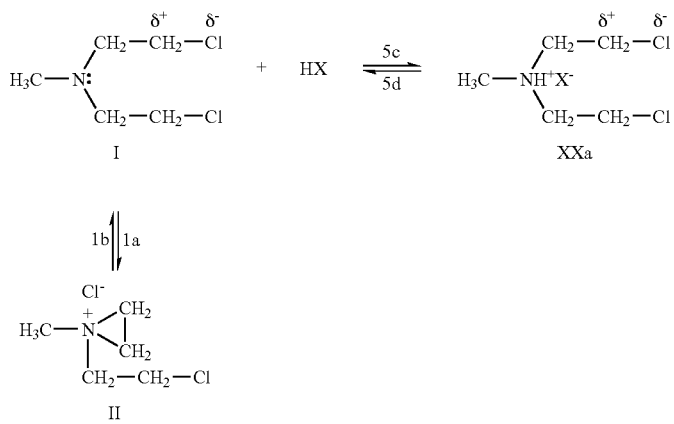

wherein R, R'. Z, Ar, L, n, and p are as defined above for the compounds of Structures (VII), (VIII), (IX), (X), (XII), (XIII), (XIV), (XV), (XVI), (XVIII), and (XIX).

In one embodiment, $X^-$ is a halide, such as $Cl^-$, $Br^-$, or $I^-$, or $HSO_4^-$ or $NO_3^-$. The corresponding HX is HCl, HBr, HI, or $H_2SO_4$, or $HNO_3$, respectively. In another embodiment, the pharmaceutically acceptable HX salt is a conventional acid-addition salt or base-addition salt formed from a non-toxic organic or inorganic acid or inorganic base. Illustrative acid- In Reactions 1a and 1b, a free form of the nitrogen mustard, structure (I), may be in equilibrium with the aziridium ion (II), as described for Reaction 1, supra. The equilibrium constant for Reactions 1a and 1b has been described as $K_{eq(1a,1b)}$, supra. In like manner, the equilibrium constant for Reactions 5a and 5b, $K_{eq(5a,5b)}$ may be expressed as the ratio of the concentration of the HX salt, (XXa), to the product of the concentration of the free base form of the nitrogen mustard, structure (I) and the concentration of HX. Therefore, in one embodiment, there may be an equilibrium concentration of aziridinium cation represented by the ratio of $K_{eq(1a,1b)}$ to $K_{eq(5a,5b)}$, even when the nitrogen mustard has been stabilized by converting the free base form of the nitrogen mustard, as represented by structure (I), infra, as illustrated by Reaction 5, to its HX salt, as represented by the structure (XXa). Therefore, the N-2 position of the guanine base of DNA, structure III in Reactions 2-4 may be alkylated by the HX salt (XXa), as in Reaction 5, because the concentration of the aziridinium cation in Reaction 5, may be a real positive number, equal to $K_{eq(1a,1b)}$ to $K_{eq(5a,5b)}$. Hereinafter, the free base form of the nitrogen mustard is any non-salt form of the nitrogen mustard, wherein a lone pair of electrons on the nitrogen atom may be available for forming the aziridinium ion, (II), as in Reaction 1, supra. In embodiments of the present invention, the aziridinium cation, Structure (II), supra, may undergo nucleophilic attack by an electron donor, resulting in alkylating the nucleophile. For example, reaction with the nucleophile guanine (G), structure (III), shown in Reaction 2, supra, at position N-7 of the guanine (G) occurs to the greatest extent. Other sites on guanine (G), and other DNA bases such as adenine (A), cytosine (C) and thymine (T), and phosphate oxygens also can be alkylated.

In another embodiment, the nitrogen mustard is provided in the form of a nitrogen mustard prodrug. Suitable nitrogen mustard prodrugs include those of the following Structure (XI):

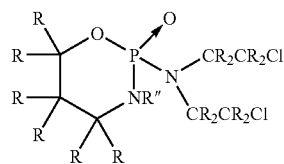

(XI)

wherein each R and each R" is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein any two R in the same molecule are optionally linked to form a three- to eight-membered cyclic group. Hereinafter, Structure (XI) may represent all racemic forms and stereoisomers wherein said compounds may be capable of optical activity.

For example, phosphatase and phosphamidase enzymes may cleave the P—N bond of Structure (XI), supra, e.g., cyclophosphamide, Structure (XIA), infra or ifosfamide, Structure (XIB), infra, resulting in an intermediate aldophosphamide, which may nonenzymatically break down to a bifunctional phosphoramide mustard, for example of Structure (XIXA) or (XIXB), as illustrated in Reactions 6a and 6b below. In an embodiment, cyclophosphamide, Structure (XIA), supra or ifosfamide, Structure (XIB), supra may be oxidatively activated by cytochrome P-450.

Reaction 6a:

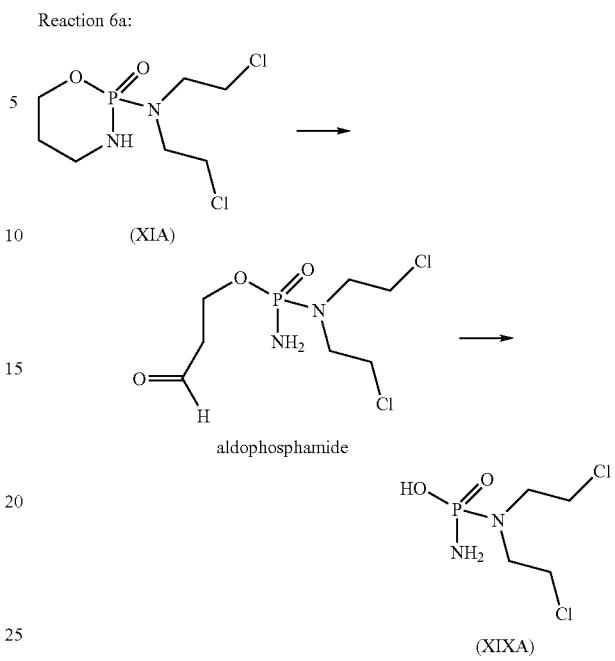

Reaction 6b:

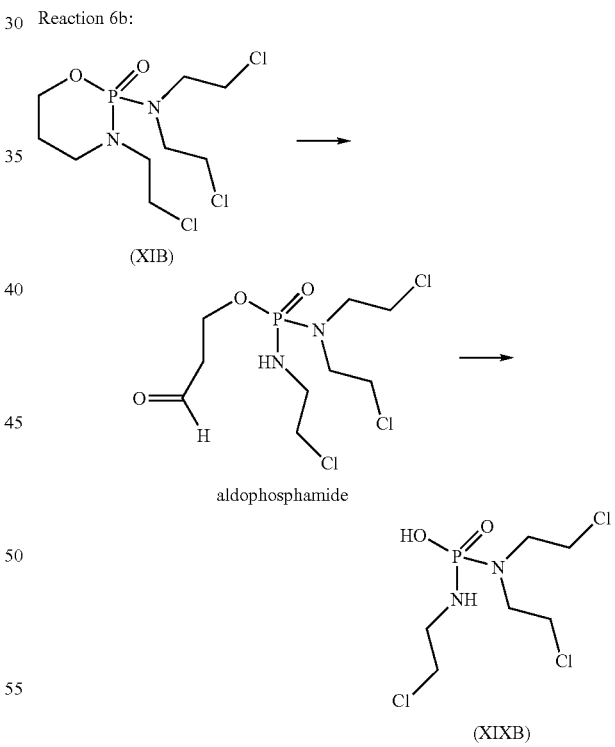

In one embodiment, the pharmaceutically acceptable excipient is a non-aqueous vehicle or carrier. In one embodiment, the non-aqueous vehicle or carrier does not include petrolatum, ethanol, or acetone. In another embodiment, the non-aqueous vehicle or carrier is present in an amount of less than 98% by weight of the composition. In another embodiment, the non-aqueous vehicle or carrier is present in an amount of about 15% to about 60% by weight of the composition.

In one embodiment, the non-aqueous vehicle or carrier comprises an ingredient selected from the group consisting of a secondary alcohol, a tertiary alcohol, an amine, an amino alcohol having 1 to 20 carbon atoms, a polypropylene glycol (PPG), a propylene glycol (PG), a polyethyleneglycol (PEG), a diethylene glycol monosubstituted ether, and a diethylene glycol monomethyl ether (DGME).

In one embodiment, the non-aqueous vehicle or carrier comprises a diethylene glycol monosubstituted ether. In another embodiment, the diethylene glycol monosubstituted ether is a compound of the formula $HOCH_2CH_2OCH_2CH_2OR^{79}$ or $(HO(CH_2CH_2O)_2R^{79})$, wherein $R^{79}$ is selected from the group consisting of a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group and an alkynylacyl group, and combinations thereof. In another embodiment, $R^{79}$ is a linear alkyl group having 1-6 carbon atoms, a branched alkyl group having 2-12 carbon atoms. In another embodiment, $R^{79}$ is a linear alkyl group having 1-6 carbon atoms. In another embodiment, $R^{79}$ is a linear alkyl group having 2 to 3 carbon atoms. In another embodiment, $R^{79}$ is ethyl, which corresponds to ethoxy diglycol reagent (also known as diethylene glycol monoethyl ether, 2-(2-ethoxyethoxy)ethanol or Transcutol®).

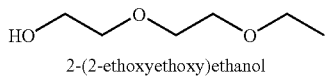

2-(2-ethoxyethoxy)ethanol

In another embodiment, the non-aqueous vehicle or carrier comprises a polyoxylglyceride. In one embodiment, the polyoxylglyceride is a caprylocaproyl, linoleoyl, oleoyl, lauroyl, or stearoyl polyoxylglyceride. In another embodiment, the polyoxylglyceride is lauroyl polyoxyl-32 glycerides, stearoyl polyoxyl-32 glycerides, medium chain triglycerides, oleoyl polyoxyl-6 glycerides, linoleoyl polyoxyl-6 glycerides, lauroyl polyoxyl-6 glycerides, or caprylocaproyl polyoxyl-8-glycerides. Such polyoxylglycerides are available from Gattefosse (Canada) under the tradenames Labrasol®, Labrafil®, and Gelucire®.

In one embodiment, the PPG has a molecular weight from about 300 to about 2500. In another embodiment, the PEG has a molecular weight from about 100 to about 5000.

In one embodiment, the secondary or tertiary alcohol is isopropyl alcohol, cetyl alcohol, stearyl alcohol, cetearyl alcohol, or lanolin alcohol.

In some embodiments, the nitrogen mustard alkylating agents disclosed herein are bifunctional alkylators, i.e., have two arms terminated with chlorine ("$CR_2CR_2Cl$") that can react, for example, with DNA to form DNA cross-links as illustrated in Reactions 1 to 4. When one arm terminated with chlorine is absent, the nitrogen mustard alkylating agent is referred to as a monofunctional alkylator or a "half-mustard."

It is believed that nucleophiles in the composition or in the environment may degrade the nitrogen mustard alkylating agent to form a nitrogen mustard degradation product by reacting with the nitrogen mustard to displace one or more terminal chlorides of the nitrogen mustard by nucleophilic substitution.

Nucleophiles are defined as molecules having electron-rich functional groups ("E"), such as —O—, —NH—, or —S—. The most nucleophilic nucleophiles are believed to be water or nucleophiles having the electron-rich functional group covalently bonded to a primary carbon atom, such as methanol or ethanol. Nucleophiles include any pharmaceutically acceptable excipient having an electron-rich functional group (E) known to the skilled artisan. Such pharmaceutically acceptable excipients include, but are not limited to, acidifying agents, adsorbants, alkalizing agents, antibacterial agents, antifoaming agents, antiseptics, antiviral agents, binding agents, buffering agents, bulking agents, chelating agents, coating agents, coloring agents, release-modifying agents, cooling agents, diluents, disintegrants, dispersing agents, emollients, emulsifying agents, film-forming agents, gelling agents, glidants, granulating agents, humectants, lubricants, ointment bases, opacifying agents, oleaginous vehicles, penetration enhancers, pH-adjusting agents, pigments, plasticizers, preservatives, refrigerants, sequestering agents, solubilizing agents, solvents, stabilizing agents, stiffening agents, surfactants, suspending agents, sweetening agents, thickening agents, transdermal delivery agents, tonicity agents, and wetting agents. Pharmaceutically acceptable excipients are described, for example, in the HANDBOOK OF PHARMACEUTICAL EXCIPIENTS (5th ed., 2006, R. C. Rowe, et al., eds.), the contents of which are herein incorporated by reference.

The degradation of a nitrogen mustard alkylating agent by a nucleophile having an electron-rich functional group is illustrated, for example, by Reactions 7a and 7b below:

Reaction 7a:

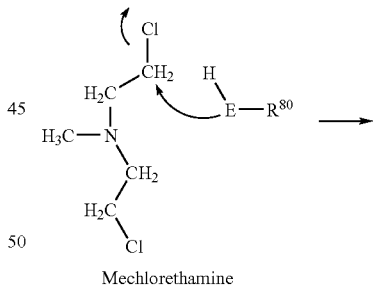

Mechlorethamine

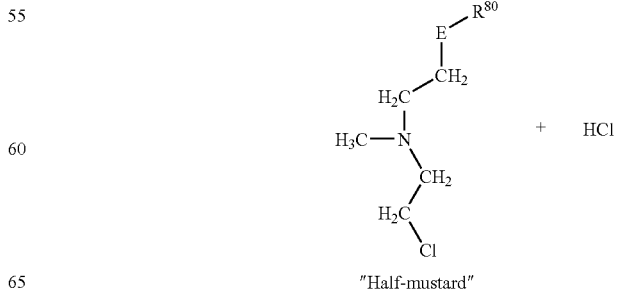

"Half-mustard"

Reaction 7b:

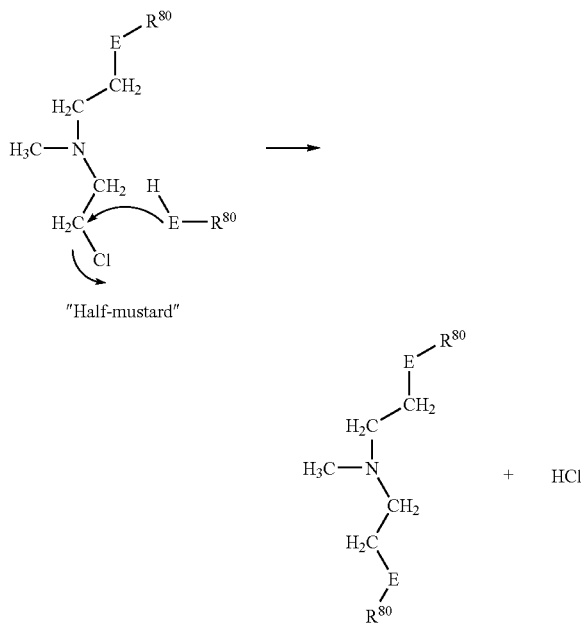

"Half-mustard"

wherein each R80 is independently a linear or branched alkyl group having 1-12 carbon atoms that is optionally substituted with one or more —COOH or —OH, and that is optionally interrupted by one or more —O—, —N—, —(CO)—, or —O—(CO)—. As used herein, the term "interrupted," when referring to an alkyl group, means that one or more of the carbon-carbon bonds of the alkyl group is replaced with a —O—, —N—, —(CO)—, or —O—(CO)—, for example, as follows:

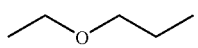

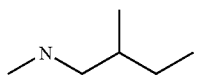

$C_5$ linear alkyl group interrupted by a —O—; $C_6$ branched alkyl group interrupted by a —N—; or

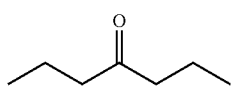

$C_7$ linear alkyl group interrupted by a —(CO)—.

It has surprisingly been found by the present inventors that such degradation reactions may be reduced and/or avoided by the presence of PEG, EG, PPG, or PG, or diethylene glycol monosubstituted ethers, such as 2-(2-ethoxyethoxy)ethanol, in the composition. Not to be limited by theory, it is believed that these excipients hydrogen bond to nucleophiles that may be present in the composition or the environment, thereby reducing the nucleophilic strength of the nucleophiles and reducing their ability to degrade the nitrogen mustard.

In another embodiment, the composition further comprises an adjuvant. Suitable adjuvants include, but are not limited to, antioxidants, preserving agents, stabilizing agents, wetting agents, emulsifying agents and the like. In other embodiments, the composition further comprises a solvent, an antioxidant, an emollient, a humectant, a preservative, an emulsifier, a pH agent, or a combination thereof.

Suitable solvents include acetone, glycols, polyurethanes, and others known in the art. Suitable emollients include mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art.

Suitable antioxidants include sodium bisulfite, butylated hydroxytoluene, edetate disodium, benzyl alcohol, ascorbic acid, citric acid, malic acid, fumaric acid, lactic acid, and propionic acid, and mixtures thereof. In one embodiment, the antioxidant is sodium bisulfite, butylated hydroxytoluene, or edetate disodium, or a mixture thereof.

Suitable humectants include glycerin, sorbitol, and others known in the art.

Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art.

Suitable pH agents include hydrochloric acid, phosphoric acid, diethanolamine, triethanolamine, sodium hydroxide, monobasic sodium phosphate, dibasic sodium phosphate, and others known in the art. Suitable pH agents also include organic acids, for example, of the formula $C_nH_{(2n+2)}COOH$, (where n is an integer of 1 to 6). Suitable organic acids include, but are not limited to, acetic acid, citric acid, tartaric acid, fumaric acid, lactic, glycolic and other alpha hydroxy acids, malic acid, carnitine, glutamic acid, aspartic acid and others known in the art. In one embodiment, the organic acid is present in am amount of about 0.01 percent to about 15 percent by weight of the composition. In another embodiment, the organic acid is present in an amount of about 1 percent to about 15 percent by weight of the composition. In another embodiment, the organic acid is present in an amount of about 2 percent to about 5 percent by weight of the composition. In one embodiment, the organic acid is present in the composition in an amount sufficient to provide a pH of less than about 7. In another embodiment, the organic acid is present in the composition in an amount sufficient to provide a pH of less than 5. In another embodiment, the organic acid is present in the composition in an amount sufficient to provide a pH of less than about 4. In another embodiment, the organic acid is present in the composition in an amount sufficient to provide a pH of about 3 to about 4. In another embodiment, the organic acid is present in an amount sufficient to provide a pH of about 2.5 to about 3.5. In another embodiment, the organic acid is present in the composition in an amount sufficient to provide a pH of about 3.

Suitable preservatives include benzyl alcohol, sodium benzoate, parabens, and others known in the art.

In one embodiment, the composition further comprises a dimethyl polysiloxane fluid. In one embodiment, the dimethyl polysiloxane fluid is a dimethicone or cyclodimethicone. In one embodiment, the dimethyl polysiloxane fluid has essentially no moisture content.

As used herein, the term "dimethicone" includes low viscosity silicones, low viscosity, i.e. from about 1 cps to about 1,000 cps at 25° C. polydimethylsiloxanes, Hexamethyldisiloxane (CAS#107-46-0), pure silicone 1 cSt, volatile silicone, volatile silicones, volatile polydimethylsiloxanes, low temperature silicones, skin care silicone, skin care silicones, Octamethyltrisiloxane (CAS#107-51-7), Decamethyltetrasiloxane (CAS#141-62-8), Dodecamethylpentasiloxane (CAS#141-63-9), trisiloxane, low viscosity dimethicone, volatile dimethicone, cosmetic dimethicone fluid, cosmetic base fluids, suntan lotion silicone, antiperspirant silicone, hair care silicone, low surface tension silicone, and low heat of vaporization silicone.

As used herein, the term "cyclomethicone" includes cyclopentasiloxane, volatile poydimethylcyclosiloxane (CAS#541-02-6), low surface tension silicone, volatile silicone, D5 silicone, Dow Corning 245 fluid, DC 245 fluid, 245 silicone, skin cream silicone, antiperspirant silicone, suntan lotion silicone, silicone for skin, skincare silicone, bodycare silicone, bath oil silicone, GE 1202, GE SF1202 cyclopentasiloxane, D5 Cyclopentasiloxane, and D5 Decamethylcyclopentasiloxane.

Generally, dimethicone and cyclomethicone are dimethyl silicone oils with good emollience, strong moisturization and humectant properties. Dimethicone and cyclomethicone have very low moisture content, as water, i.e. <0.1% by weight because they are methyl stopped instead of OH stopped polymers.

In one embodiment of the invention, the composition comprises an alkylating agent or a pharmaceutically acceptable salt thereof, and a pharmaceutically acceptable excipient selected from the group consisting of 2-(2-ethoxyethoxy) ethanol, Hydroxypropylcellulose, Menthol Crystals USP, Butylated Hydroxytoluene NF, Glycerin USP, Edetate Disodium USP, Decyl Methyl Sulfoxide, Kris-Ester 236 and combinations thereof.

In one embodiment, the composition does not include any grade of white or yellow petrolatum recognized in the art as suitable for human application. In another embodiment, the non-aqueous vehicle or carrier does not include material commercially available as Penreco Snow White Pet USP. In another embodiment, the composition does not include hydrocarbon mixtures formulated with mineral oils in combination with paraffin waxes of various melting points. In another embodiment, the composition does not include a lipophilic emollient selected from the group consisting of: petrolatum; and esters of fatty acids.

In some embodiments, the composition does not comprise an inorganic salt. In other embodiments, the composition does not comprise an antioxidant.

In one embodiment, the composition does not comprise water or ethanol. In some embodiments, the composition comprises less than about 15% by weight water, less than about 10% by weight water, less than about 5% by weight water, or less than about 1% by weight water. In other embodiments, the composition comprises less than about 15% by weight ethanol, less than about 10% by weight ethanol, less than about 5% by weight ethanol, or less than about 1% by weight ethanol. In one embodiment, the composition does not comprise petrolatum. In some embodiments, the composition comprises less than about 15% by weight petrolatum, less than about 10% by weight petrolatum, less than about 5% by weight petrolatum, or less than about 1% by weight petrolatum. In some embodiments, the composition comprises less than about 15% by weight acetone, less than about 10% by weight acetone, less than about 5% by weight acetone, or less than about 1% by weight acetone.

In one embodiment, the pH of the composition is less than about 7. In another embodiment, the pH of the composition is less than 5. In another embodiment, the pH of the composition is less than about 4. In another embodiment, the pH of the composition is about 3 to about 4. In another embodiment, the pH of the composition is about 2.5 to about 3.5. In another embodiment, the pH of the composition is about 3.

In one embodiment, the viscosity of the composition is more than the viscosity of water (about 1 cps) and less than the viscosity of petrolatum (about 64,000 cps). In another embodiment, the viscosity of the composition is about 5,000 cps to about 50,000 cps. In another embodiment, the viscosity of the composition is about 15,000 cps to about 40,000 cps. In another embodiment, the viscosity of the composition is about 20,000 cps to about 35,000 cps. In another embodiment, the viscosity of the composition is about 25,000 cps to about 35,000 cps. Viscosity can be measured with a Brookfield programmable rheometer, model RVDV-III with cone plate configuration using spindle CPE52, or equivalent apparatus. Viscosity measurements can be taken at 25° C. and 1 rpm over a period of 5-10 minutes, using a 0.5 mL sample size.

In one embodiment, the composition has a duration of activity from about 3 months to about 3 years.

In one embodiment, the composition is stable, i.e., at least about 80% of the alkylating agent is present in the composition or less than about 20% by weight degradation product of the alkylating agent is present in the composition after storage. In one embodiment, the composition is stored at a temperature of at least about −20° C. In another embodiment, the composition is stored at a temperature of about −20° C. to about −10° C. In one embodiment, the composition is stored at a temperature of at least about 2° C. In another embodiment, the composition is stored at a temperature of about 2° C. to about 8° C. In another embodiment, the composition is stored at room temperature. In another embodiment, the composition is stored at about 25° C. In another embodiment, the composition is stored for about 3 months to about 3 years.

In one embodiment, at least about 80% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, at least about 85% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, at least about 90% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, at least about 95% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, at least about 98% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, at least about 99% of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months.

In one embodiment, less than about 20% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, less than about 15% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, less than about 10% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, less than about 5% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, less than about 1% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In one embodiment, less than about 0.5% by weight degradation product of the alkylating agent is present in the composition after storage for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months.

In one embodiment, the composition is stored in a glass vial sealed from the atmosphere. In another embodiment, the composition is stored in an amber vial sealed from the atmosphere. In another embodiment, the composition is stored in an aluminum foil-lined container. In another embodiment, the composition is stored in an aluminum foil tube. In another embodiment, the composition is stored in a plastic container. In another embodiment, the composition is stored in a polypropylene container.

In one embodiment, the composition is stable in the presence of water. In another embodiment, the composition is stable and comprises 1%, 2%, 5%, 10%, 15%, or 20% by weight water.

In one embodiment, the alkylating agent is a nitrogen mustard and the degradation product is a nitrogen mustard degradation product.

In some embodiments, the nitrogen mustard degradation product is a half-mustard. In some embodiments, the half-mustard has the following structure (DP-A) or (DP-B):

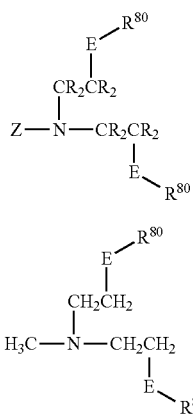

wherein:
Z is a linear alkyl group having 1-6 carbon atoms;
each R is independently hydrogen or a linear alkyl group having 1-6 carbon atoms;
each E is independently —O—, —NH—, or —S—; and
each $R^{80}$ is independently a linear or branched alkyl group having 1-12 carbon atoms that is optionally substituted with one or more —COOH or —OH, and that is optionally interrupted by one or more —O—, —N—, —(CO)—, or —O—(CO)—.

In some embodiments, the moiety E-$R^{80}$ is

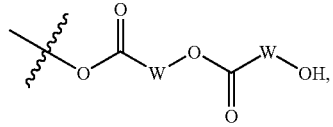

wherein W is a linear or branched alkyl group having 1-6 carbon atoms that is optionally substituted with —COOH. In another embodiment, the moiety E-$R^{80}$ is

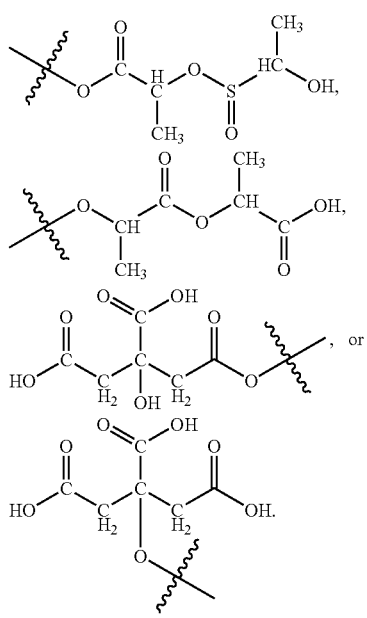

In one embodiment, the moiety E-$R^{80}$ is

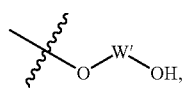

wherein W' is a linear or branched alkyl group having 1-6 carbon atoms. In another embodiment, the moiety E-$R^{80}$ is

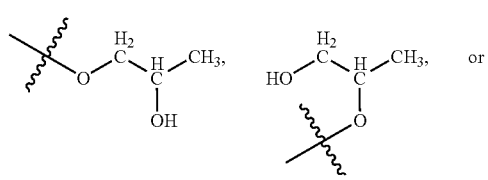

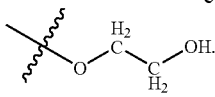

In other embodiments, the half-mustard has the structure (DP-A) or (DP-B), wherein Z is a linear alkyl group having 1-6 carbon atoms; each E is independently —O—, —NH—, —S—; —OC(O)CH(CH$_3$)OC(O)CH(CH$_3$)—; —OCH(CH$_3$)C(O)OCH(CH$_3$)—; or —O(CH$_2$)$_2$O(CH$_2$)$_2$O—; and each R$^{80}$ is independently a linear or branched alkyl group having 1-12 carbon atoms, —COOH, or —OH.

In other embodiments, the nitrogen mustard degradation product has the following structure (DP-C) or (DP-D):

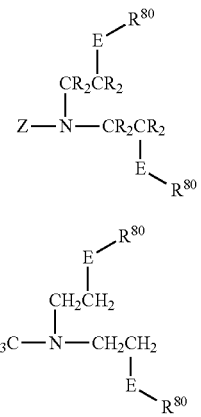

wherein:

Z is a linear alkyl group having 1-6 carbon atoms;

each R is independently hydrogen or a linear alkyl group having 1-6 carbon atoms;

each E is independently —O—, —NH—, or —S—; and each R$^{80}$ is independently a linear or branched alkyl group having 1-12 carbon atoms that is optionally substituted with one or more —COOH or —OH, and that is optionally interrupted by one or more —O—, —N—, —(CO)—, or —O—(CO)—.

In some embodiments, each E-R$^{80}$ moiety is independently

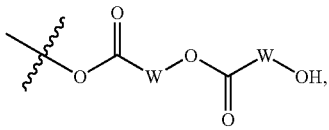

wherein W is a linear or branched alkyl group having 1-6 carbon atoms that is optionally substituted with —COOH. In another embodiment, the each E-R$^{80}$ moiety is independently

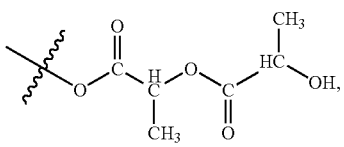

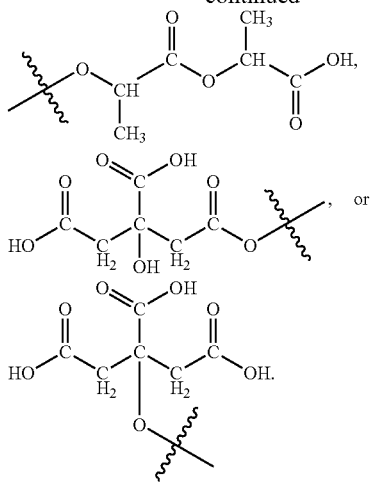

In one embodiment, each E-R$^{80}$ moiety is independently

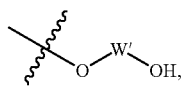

wherein W' is a linear or branched alkyl group having 1-6 carbon atoms. In another embodiment, each E-R$^{80}$ moiety is independently

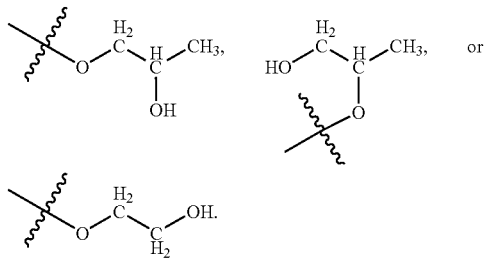

In other embodiments, nitrogen mustard degradation product has the structure (DP-C) or (DP-D), wherein Z is a linear alkyl group having 1-6 carbon atoms; each E is independently —O—, —NH—, —S—; —OC(O)CH(CH$_3$)OC(O)CH(CH$_3$)—; —OCH(CH$_3$)C(O)OCH(CH$_3$)—; or —O(CH$_2$)$_2$O(CH$_2$)$_2$O—; and each R$^{80}$ is independently a linear or branched alkyl group having 1-12 carbon atoms, —COOH, or —OH.

III. METHODS FOR STABILIZING ALKYLATING AGENTS

In one embodiment, the invention provides methods for stabilizing an alkylating agent comprising combining the alkylating agent with a pharmaceutically acceptable excipient to provide a stable composition of the alkylating agent.

In one embodiment, the alkylating agent is a nitrogen mustard. In another embodiment, the alkylating agent is a nitrogen mustard of Structure (VII), (VIII), (IX), (X), (XII), (XIII), (XIV), (XV), (XVI), (XVII), (XVIII) or (XIX). In another embodiment, the nitrogen mustard is bis-(2-chloroethyl)ethylamine, bis-(2-chloroethyl)methylamine, or tris-(2-chloroethyl)amine. In another embodiment, the nitrogen mustard is bis-(2-chloroethyl)methylamine.

In one embodiment, the pharmaceutically acceptable excipient is polypropylene glycol (PPG), propylene glycol (PG), polyethylene glycol (PEG), ethylene glycol (EG), or 2-(2-ethoxyethoxy)ethanol. In another embodiment, the pharmaceutically acceptable excipient is 2-(2-ethoxyethoxy)ethanol. In another embodiment, the pharmaceutically acceptable excipient consists essentially of Propylene Glycol, 2-(2-ethoxyethoxy)ethanol, Hydroxypropylcellulose, Menthol Crystals USP, Butylated Hydroxytoluene NF, Glycerin USP, Edetate Disodium USP, Decyl Methyl Sulfoxide, and Kris-Ester 236. In another embodiment, the pharmaceutically acceptable excipient consists essentially of Hydroxypropylcellulose, Edetate Disodium, Menthol, Butylated Hydroxytoluene, 2-(2-ethoxyethoxy)ethanol, Isopropyl Alcohol, Propylene Glycol, Glycerin, Lactic Acid, and Sodium Chloride.

In one embodiment, the combining comprises mixing. The mixing may be accomplished by various means, including flocculation, wetting, levigation, trituration, stirring, blending, homogenizing, sonication, injection, countercurrent exchange, impinging jet mixing, expansion of a supercritical fluid, and milling. As used herein, "levigation" is defined as the grinding to a powder of a moist or hard substance, or the mixing of a solid or particulate substance together with a solvating or wetting agent, thereby intimately mixing or coating the solid or particulate with the solvating or wetting agent.

In another embodiment, the invention provides methods for stabilizing an alkylating agent comprising: (a) providing a non-aqueous flowable ointment or cream, wherein the non-aqueous flowable ointment or cream does not include petrolatum, ethanol, or acetone; (b) combining an alkylating agent or pharmaceutically acceptable HX salt of an alkylating agent with a solvent that does not include petrolatum, ethanol, or acetone; and (c) combining the non-aqueous flowable ointment or cream of step (a) with the alkylating agent or pharmaceutically acceptable HX salt of the alkylating agent in the solvent of step (b).

In one embodiment, the method produces a composition of alkylating agent or pharmaceutically acceptable HX salt of the alkylating agent having a duration of activity from about 3 months to about 3 years. In another embodiment, the method produces a composition of alkylating agent or pharmaceutically acceptable HX salt of the alkylating agent having a duration of activity from about 3 months to about 5 years.

The type of container in which the compositions of the invention are stored may also affect the stability of the alkylating agents. The inventors disclose that lower volume containers having from about 0.01 to about 0.2 ml, from about 0.1 to about 0.5 ml, or from about 0.1 to about 1 ml may advantageously be used to provide from 1 to 10 applications of the pharmaceutically acceptable alkylating agent (such as Nitrogen Mustard.HCl) over a shorter period of use than the 50 ml flip top plastic cylinders, so that lower amounts of nucleophiles such as ambient water or other ambient nucleophiles such as methanol or ethanol may be introduced into the lower volume containers than when the flip top plastic cylinder is opened to the ambient environment over a period of 100 to 1000 applications. The inventors anticipate decreased decomposition of the free base form of nitrogen mustard or its HX salt, when the nitrogen mustard is contained in lower volume containers intended for from about 1 to 10 applications. In theory, the chlorides of the free base form of the nitrogen mustard or its HX salt may be displaced by nucleophilic attack, such as by water or ethanol, resulting in substitution of the Cl by an OH. Said decomposition of the free form of the nitrogen mustard or its HX salt may be avoided by isolating the nitrogen mustard from traces of water, ethanol or other nucleophiles in the environment. An apparatus 20, as depicted in FIG. 2, infra, depicts this smaller volume container.

Figure 2:
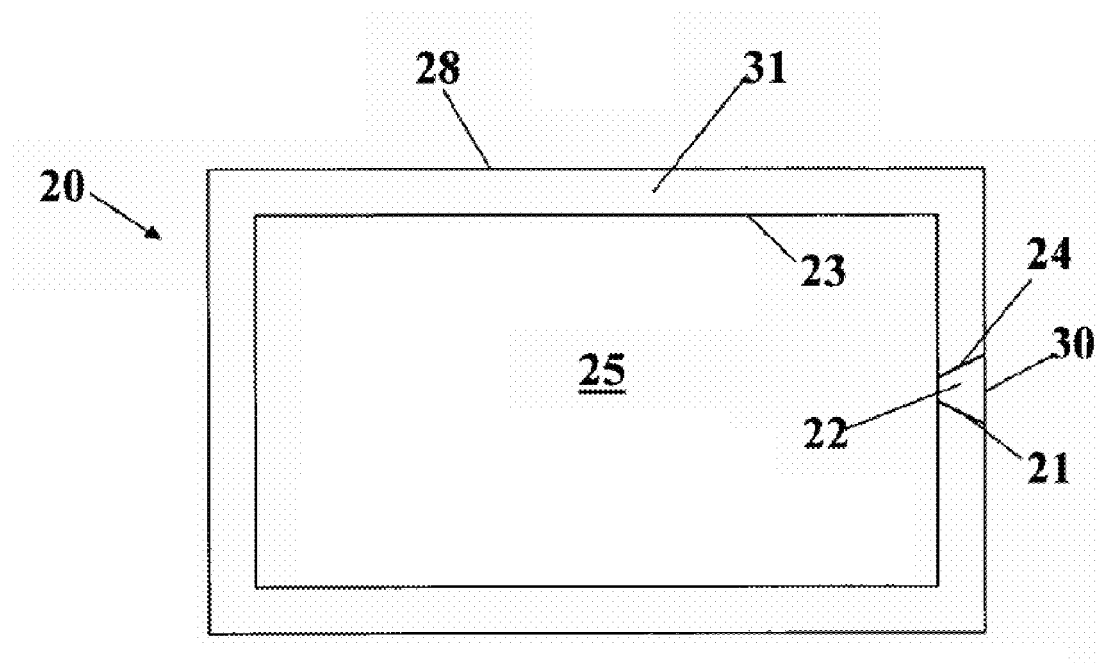
FIGS. 2-4 illustrate a front cross-sectional view of an apparatus having a first compartment, in accordance with embodiments of the present invention.

FIG. 2 depicts a front cross-sectional view of the apparatus 20 for containing the compositions of the invention, comprising: a compartment 25 enclosed by a wall 31. The wall 31 comprises an outer surface 28 and an inner surface 23, ends 24 and 21, and opening 30. The first compartment 25 may be charged with the essentially completely uniform mixture of the composition through the opening 30. The opening 30 may be closed with plug 22. The plug 22 may be made of the same material as the wall 31, or a lower melting plastic or wax material.

Figure 3:
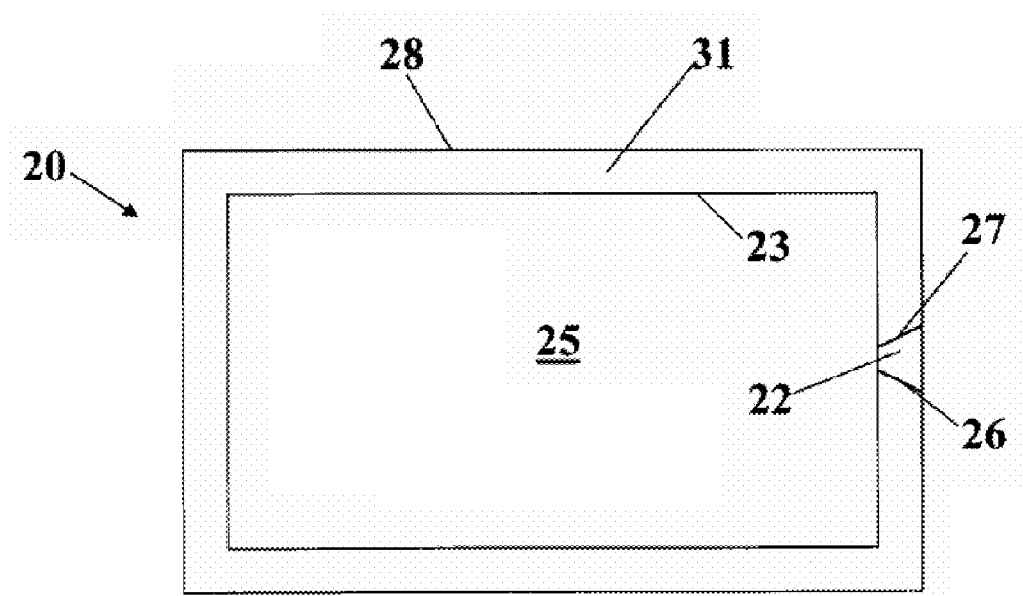

FIG. 3 depicts the apparatus 20, after forming heat seals 26 and 27 by heating the plug 22 and the ends 21 and 24 to their melting points, wherein heating physically and mechanically couples ends 21 and 24 to form mechanically strong heat seals 26 and 27.

Figure 4:
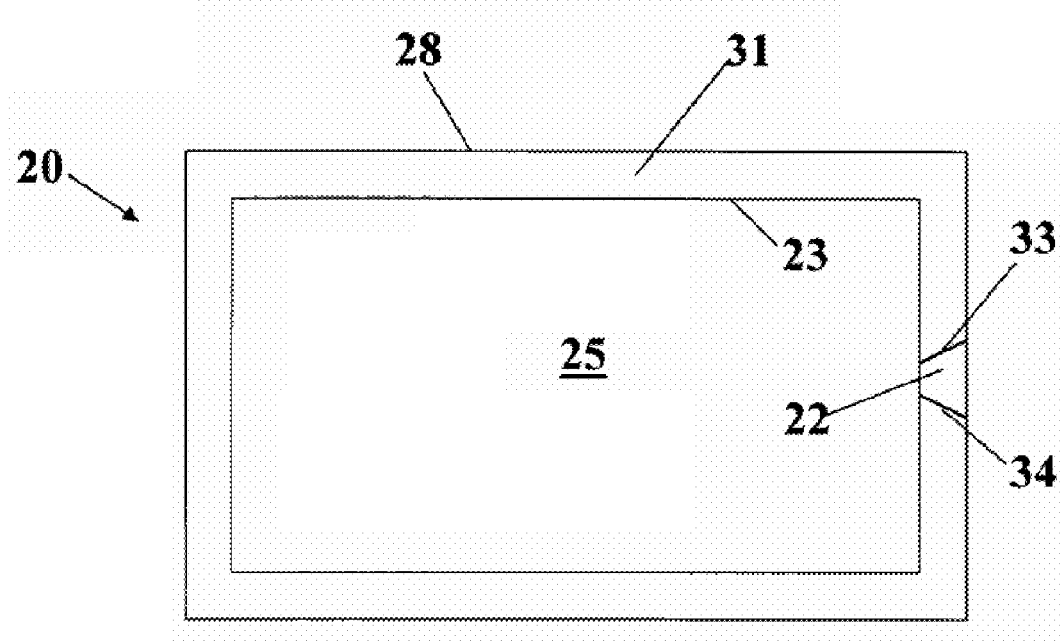
Figure 5:
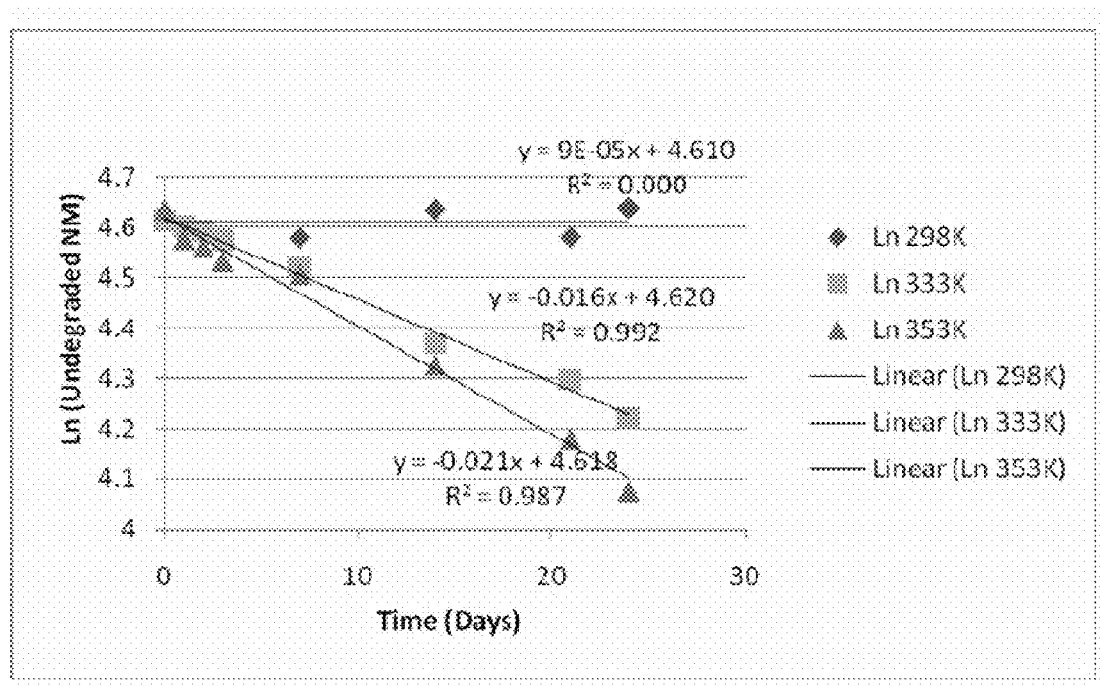
FIG. 5 depicts a Log-linear plot of the stability of mechlorethamine hydrochloride (MCHCl) in 2-(2-ethoxyethoxy) ethanol at various temperatures over time, in accordance with embodiments of the present invention.

FIG. 4 depicts the apparatus 20, after forming serrated perforations 33 and 34 in the plug 22 using a crimping tool or other appropriate device for forming serrated perforations 33 and 34. The serrated perforations 33 and 34 weaken the heat seals 21 and 24 so that they become mechanically less strong, resulting in a tear line for removal of the plug 22 by the patient seeking to apply the composition to a diseased area or area for treatment. In one embodiment, a person wishing to apply the composition to the diseased area or area for treatment may remove plug 22 from the wall 31 of the apparatus 20, restoring the opening 30 in the wall 31 so squeezing or applying pressure to the wall 31 reduces the volume of the apparatus 20, resulting in the composition flowing outward through opening 30 to be applied to the diseased area or area for treatment.

In one embodiment, the nitrogen mustard alkylating agent is present in the composition in the compartment 25 in an amount of about 1 mg to about 2000 mg per 100 mL of the composition; about 10 mg to about 40 mg per 100 mL of the composition; or about 15 mg to about 30 mg per 100 mL of the composition. An orifice or opening 30 may be made by forming an opening in the outer wall 31, through which opening 30 the composition is then provided by prescription of a physician for treatment of the patient.

The outer wall 31 of apparatus 20 is impermeable to the mixture of step g) or step 9), supra, and/or the reconstituted nitrogen mustard solutions. The wall 31 may be made from elastomeric materials including ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinylchloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylenevinyloxyethanol copolymer; silicone copolymers, polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers polysiloxane-ethylene copolymers, polysiloxane-alkylenesilane copolymers, polysiloxaneethylenesilane copolymers, cellulose polymers, methyl cellulose, ethyl cellulose, hydroxypropyl methyl cellulose, cellulose esters, polycarbonates, polyesters, polytetrafluoroethylene, starches, gelatins, natural gums, synthetic gums, and combinations thereof.

In one particular embodiment, the invention provides methods for stabilizing nitrogen mustard alkylating agents by combining them with the pharmaceutically acceptable excipient 2-(2-ethoxyethoxy)ethanol.

Nitrogen mustard alkylating agents, such as MCHCl, are recognized by those of ordinary skill in the art to rapidly degrade to inactive products in the presence of base, water and many pharmaceutical excipients, including primary alcohols such as ethanol. As such, most MCHCl topical formulations currently employed for the treatment of dermatological conditions are composed of MCHCl dispersed in hydrophobic excipients, such as petrolatum, mineral oil and other lipophilic substances. These products tend to be stiff, have a high skin drag, and leave an adhesive, greasy layer on the skin that may also stain clothing or rub off on others, characteristics not generally acceptable to patients.

Formulation of these products is generally accomplished by mixing MCHCl powder directly into these viscous substances. Thus, the homogeneous incorporation and distribution of the dry powder into the oleaginous vehicle is complicated by clumping, sticking and caking of the dry powder in the vehicle, thereby requiring extensive mixing and homogenizing, as well as levigation and wetting agents not necessarily desirable in the final product. In addition, current formulation methods require repeated handling of the highly poisonous MCHCl powder, which is easily swept up and dispersed in the air, thereby posing a serious contamination risk for both personnel and the manufacturing facility.

Alternative topical formulations employing less lipophilic and amphipathic excipients have been explored. These excipients include 2-(2-ethoxyethoxy)ethanol, marketed under various trade names, including 2-(2-ethoxyethoxy) ethanol and diethylene glycol monoethyl ether. Although 2-(2-ethoxyethoxy)ethanol has served as an effective vehicle for many drugs, it is a primary alcohol, and many commercial forms of this excipient contain significant amounts of water and other potentially nucleophilic and solvolytic impurities, including the primary alcohols 2-methoxyethanol and 2-ethoxyethanol.

The inventors report, however, that MCHCl may be dispersed in 2-(2-ethoxyethoxy)ethanol across a wide range of concentrations while remaining stable for extended periods of time across a wide temperature range, even though 2-(2-ethoxyethoxy)ethanol is a primary alcohol. MCHCl remains stable when dispersed in commercial 2-(2-ethoxyethoxy) ethanol containing 0.1% w/w or more of water, which generally promotes solvolysis of this nitrogen mustard. The inclusion of stabilizing agents, such lactic acid or sodium chloride, has no significant effect on nitrogen mustard stability in the dispersion, and is not necessary for preparing a stable dispersion. Notably, MCHCl remains completely stable when dispersed in 2-(2-ethoxyethoxy)ethanol for over three months at room temperature. Significant degradation of MCHCl in the dispersion is only noted at elevated temperatures. Indeed, less than ten percent of the MCHCl in such a dispersion degraded after storage at temperature as high as 80° C. for an entire week. (See Example 7 below).

That MCHCl remains stable in the presence of the primary alcohol 2-(2-ethoxyethoxy)ethanol and water, and without stabilizers, preservatives or cooling agents, is particularly surprising, as it is known that MCHCl readily undergoes rapid solvolysis and nucleophilic substitution when in contact with many primary alcohols, water and mixtures thereof. This unexpected result, wherein MCHCl, known to be readily degraded in the presence of water and primary alcohols, and at elevated temperatures, remained stable in a 2-(2-ethoxyethoxy)ethanol dispersion for long periods of time at practical working temperatures, is neither obvious nor predictable, and underscores the novelty and utility of such a dispersion and its applications and uses. Indeed, since the pKa of 2-(2-ethoxyethoxy)ethanol and the alkoxy alcohol impurities in 2-(2-ethoxyethoxy)ethanol is lower than that of ethanol, they are theoretically even more nucleophilic than ethanol. Nevertheless, MCHCl, normally labile when exposed to such compounds, is quite stable in this dispersion.

IV. METHODS FOR TREATING SKIN DISORDERS

In one embodiment, the invention encompasses methods for treating a skin disorder comprising topically administering to a subject in need thereof a stable composition comprising an effective amount of an alkylating agent or a pharmaceutically acceptable salt, solvate, or prodrug thereof, and at least one pharmaceutically acceptable excipient.

In one embodiment, the alkylating agent is a nitrogen mustard. In another embodiment, the alkylating agent is a nitrogen mustard of Structure (VII), (VIII), (IX), (X), (XII), (XIII), (XIV), (XV), (XVI), (XVII), (XVIII) or (XIX). In another embodiment, the nitrogen mustard is bis-(2-chloroethyl) ethylamine, bis-(2-chloroethyl)methylamine, or tris-(2-chloroethyl)amine. In another embodiment, the nitrogen mustard is bis-(2-chloroethyl)methylamine.

An illustrative embodiment of the method is depicted in FIG. 1. FIG. 1 depicts a method 1, for treating a person with a skin disorder, comprising: a step 10, topically applying to the affected skin a nitrogen mustard or a pharmaceutically acceptable HX salt of the Nitrogen Mustard, wherein the nitrogen mustard or the pharmaceutically acceptable HX salt of the Nitrogen Mustard is in a non-aqueous vehicle or carrier that does not include petrolatum, ethanol, or acetone.

In one embodiment, the skin disorder is a T-cell mediated skin disorder. In one embodiment, the T-cell mediated skin disorder is psoriasis, actinic keratosis, cutaneous T-cell lymphoma, cutaneous B-cell lymphoma, mycosis fungoides, alopecia, alopecia areata, or vitiligo.

In one embodiment, the skin disorder is psoriasis, eczema, actinic keratosis, lupus, sarcoidosis, alopecia, alopecia areata, cutaneous T-Cell lymphoma, i.e., mycosis fungoides, lymphoreticular neoplasia, pleural or peritoneal effusions, cutaneous B-cell lymphoma, pseudolymphoma of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease (PLEVA), or vitiligo.

In one embodiment, patients having mycosis fungoides (MF) topically treated with nitrogen mustard compounded into a polypropylene glycol (PPG, molecular weight from about 300 to about 2500), propylene glycol (PG), polyethyleneglycol (PEG, molecular weight from about 100 to about 1000) or ethylene glycol ointment or cream showed no evidence of any systemic toxicities.

Table 1 below provides a summary of topical treatment of patients having MF with a nitrogen mustard composition A, as described in Table 2 below (containing propylene glycol (PG)), including response rates and toxicities.

TABLE 1

Composition A in Mycosis Fungoides (MF): Summary of Clinical Outcomes and Toxicities

| No. of patients | Follow-up (yrs) | Vehicle | Dose | % Complete response | % Partial Response | % Hyper-sensitivity reactions | % Systemic Toxicities* |
|---|---|---|---|---|---|---|---|
| 14 | <1 | Propylene glycol | 10 mg % topically applied once daily | 36% | 42% | 7% | 0% |

*Systemic toxicities monitored by serial History & Physicals laboratory studies

Systemic Absorption

There is no evidence of any clinically significant systemic absorption of topically applied nitrogen mustard. No systemic toxicities from percutaneous absorption have been observed in long-term topical nitrogen mustard use in MF.

Genetic toxicity—No genetic toxicity has been observed with the use of topical nitrogen mustard application. This is best documented in a study that demonstrated no effect on sister-chromatid exchanges in the peripheral blood lymphocytes of CTCL-MF patients assayed before and after topical nitrogen mustard treatment.

Bone Marrow Suppression—No evidence of bone marrow suppression (anemia, leukoopenia or thrombocytopenia) has reported with long term use of topical nitrogen mustard, based on serial monitoring of the complete blood count.

Heptatotoxicity—No evidence of hepatotoxicty has reported with long term use of topical nitrogen mustard, based on serial monitoring of peripheral blood liver function tests.

Nephrotoxicity—No evidence of nephrotoxicity has been reported with long term use of topical nitrogen mustard, based on serial monitoring of peripheral blood renal function tests.

Environmental Contamination

Minimal evidence of environmental contamination has been demonstrated with topical nitrogen mustard use.

Cutaneous Side Effects

Hyperpigmentation—resulting from the direct melanogenic effects of nitrogen mustard, has been reported in a large percentage of treated patients. The hyperpigmentation is reversible and decreases gradually in most patients, even if topical therapy is continued.

Contact dermatitis—is a common complication of topical nitrogen mustard application. An irritant contact dermatitis is most common and can be seen in up to 25% of individuals using topical nitrogen mustard ointment, particularly if used in sensitive areas such as the face or skin folds. Allergic contact dermatitis is also observed with topical nitrogen mustard use.

Immediate-type (urticarial) reactions—are rare.

Allergic contact dermatitis—from delayed-type hypersensitivity (DTH) reactions is more common and appears to be dose-dependent. Higher concentrations of aqueous preparations are associated with a DTH frequency of 10-67%. Desensitization with lower concentrations of nitrogen mustard has been successfully employed in patients with DTH reactions to nitrogen mustard. The use of a lower concentration ointment preparation dramatically reduces the incidence of DTH reactions. Stanford University reported 0% DTH reactions in patients using nitrogen mustard ointment for the first time and an 8% frequency of DTH in patients with a previous history of HN hypersensitivity, in their series utilizing a nitrogen mustard ointment preparation.

Pediatric Use

Topical nitrogen mustard has been reported to be used in children and adolescents (<18 years) without any significant differences in toxicities than in adults.

Use in Pregnancy

Despite the lack of evidence of percutaneous absorption of topical nitrogen mustard, the use of topical nitrogen mustard has historically been avoided in pregnant and nursing women.

Cutaneous Carcinogenesis

There are no reports of a significantly increased incidence of squamous cell carcinoma (SCC) of the skin with prolonged use of topical nitrogen mustard. Several groups have reported an approximately 10% (4%-14%) frequency of SCC in CTCL-MF patients using topical nitrogen mustard and suggest a potential risk of epidermal carcinogenesis. These retrospective studies, however, do not account for confounding variables, such as CTCL-MF associated risk for second malignancies, prior therapies (e.g. radiation therapy to the skin), and do not have adequate control groups.

The rationale for the use of topical nitrogen mustard for the treatment of vitiligo lies in the clinical and experimental observations that nitrogen mustard produces cutaneous hyperpigmentation not associated with an inflammatory response. It has long been observed that the treatment of MF with topical nitrogen mustard produces hyperpigmentation. The same phenomenon has been reported in nitrogen mustard treatment of psoriasis. Indeed, the inventors disclose successful regimentation of vitiligo treated with topical nitrogen mustard has been demonstrated. Supporting the direct effect of nitrogen mustard on melanogenesis, the pigmentation of hairless mice in response to topical nitrogen mustard. In humans, ultra structure studies demonstrate topical NM increases melanosome numbers and distribution without toxic effects to epidermal microenvironment.

In one embodiment, the composition of alkylating agent is topically administered to humans or animals in the form of a sterile solution or suspension that contains a suitable quantity of alkylating agent. In one embodiment, the composition comprises an effective amount of alkylating agent. In some embodiments, the topical solution or suspension is incorporated in a slow release non-aqueous matrix for administering transdermally.

In one embodiment, the composition is topically administered to the subject once daily. In another embodiment, the composition is topically administered to the subject twice daily. In another embodiment, the composition is topically administered to the subject every other day, every third day, every fourth day, every fifth day, every sixth day, or once weekly.

In some embodiments, the effective amount of alkylating agent is about 1 ng to about 40 mg per 1.9 $m^2$ per day, about 10 ng to about 10 mg per 1.9 $m^2$ per day, or about 100 ng to about 4 mg per 1.9 $m^2$ per day. In other embodiments, the effective amount of alkylating agent is about 0.5 ng to about 20 mg per m² per day, about 5 ng to about 5 mg per m² per day, or about 50 ng to about 2 mg per m² per day.

In other embodiments, the effective amount of alkylating agent is about 1 ng to about 40 mg per 60 kg per day, about 10 ng to about 10 mg per 60 kg per day, or about 100 ng to about 4 mg per 60 kg per day. In other embodiments, the effective amount of alkylating agent is about 0.02 ng to about 0.7 mg per kg per day, about 0.2 ng to about 0.2 mg per kg per day, or about 1.7 ng to about 0.07 mg per kg per day.

In some embodiments of the methods, the composition contains a vehicle or carrier that ameliorates skin irritation that can result from administration of the nitrogen mustard, pharmaceutically acceptable salt of the nitrogen mustard, or nitrogen mustard prodrug. In some embodiments, the composition is effective to treat the skin disorder, but does not cause hypersensitivity reactions.

In another embodiment, the compositions of the invention can be used as adjunct therapy in combination with existing therapies, such as for hyperthermia or in the management of cancer treatment in patients having cancer. In one embodiment, the invention encompasses a method for treating a T-cell mediated skin disorder comprising administering a nitrogen mustard and another therapeutic agent.

V. OTHER USES

The compositions of the invention have a number of additional uses and applications, such as formulation aids and as concentrated sources of alkylating agents for dilution and incorporation into a variety of dispersed systems and pharmaceutical products.

In one embodiment, the invention encompasses methods of using the above-described compositions as a formulation aid, as and as a means of storing, transporting, and dispensing discrete quantities of an alkylating agent for use in pharmaceutical formulations and other preparations. In one embodiment, the composition comprises an alkylating agent dispersed in 2-(2-ethoxyethoxy)ethanol.

In another embodiment, the invention encompasses an alkylating agent or agents dispersed in 2-(2-ethoxyethoxy)ethanol for use as a formulation aid, where said formulation aid is employed as a dispersion of a pharmaceutically acceptable alkylating agent or mixture of alkylating agents for subsequent dispersion and dilution into a bulk pharmaceutical product during the formulation and manufacture of said product.

As a formulation aid, the composition can serve as a pre-solvated, pre-dispersed form of an alkylating agent for ready dispersion and homogeneous mixing into a pharmaceutical formulation or other preparation, such as a solution, a suspension, an ointment, a cream, a lotion, a plaster, a spray, a colloid and a paste. Such a pre-dispersed form of an alkylating agent, already de-gassed and solvated, facilitates homogeneous mixing into such dosage forms while minimizing or eliminating clumping, flocculation, agglomeration, sticking and caking of alkylating agents.

The composition can be stored in any suitable container, such as a jar, a bottle, a flask, a bag, a collapsible bag, a bladder, a syringe, a collapsible tube or a drum. Said container might also have an appropriate dispensing port, such as a mouth, a spigot, a valve, a syringe port, and a pump. Said container might also be pressurized, or be charged by or attached to an inert gas source, such as dry nitrogen or helium, in order to further maintain stability of the dispersion and replace the dispensed volume of the dispersion with inert gas.

In another embodiment, the invention encompasses a method of formulating a pharmaceutical product, a component of which is at least one hydrolytically unstable alkylating agent(s), comprising: providing a formulation aid, wherein said formulation aid is a pre-solvated or pre-dispersed form of the alkylating agent; and dispersing the formulation aid into a pharmaceutical formulation or other preparation, wherein the formulation aid and the pharmaceutical formulation are substantially homogeneous. In one embodiment, the alkylating agent is a nitrogen mustard. In one embodiment, the formulation aid is 2-(2-ethoxyethoxy)ethanol.

In another embodiment, the invention encompasses a method for preparing a composition comprising an alkylating agent or a pharmaceutically acceptable salt, solvate, or prodrug thereof, and a pharmaceutically acceptable excipient, comprising: combining the alkylating agent or pharmaceutically acceptable salt, solvate, or prodrug thereof and the pharmaceutically acceptable excipient.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1

Preparation of a Topical Ointment Comprising Bis-(2-chloroethyl)methylamine Hydrochloride in a Pharmaceutically Acceptable Vehicle or Carrier (a) Composition of the Topical Ointment The components/composition of the topical ointment is provided in the following Table 2.

TABLE 2

| Composition A | | |
|---|---|---|
| Ingredient | Amount per 100 mL | Percent |
| PPG, PG, PEG, or EG, USP | 15-60 mL | 15-60% |
| 2-(2-ethoxyethoxy)ethanol | 15-60 mL | 15-60% |
| Hydroxypropylcellulose, NF (1500 cps) | 0.75 g | 0.75% |
| Menthol crystals, USP | 0.08 g | 0.08% |
| Butylated hydroxytoluene, NF (BHT) | 0.05 g | 0.05% |
| Glycerin, USP | 12.75 mL | 12.75% |
| Edetate disodium, USP | 0.05 g | 0.05% |
| Decyl methyl sulfoxide | 0.125 g | 0.13% |
| Kris-Ester 236 liquid | 5 g | 5.00% |
| Alcohol anhydrous 100% SDA 3A | 2.175 mL | 2.18% |
| Bis-(2-chloroethyl)methylamine HCl[b] | 0.001-2 g | 0.001-2.0% |

[a] Available from Merck & Co., West Point, PA 19486

(b) Manufacturing

The topical ointment may be manufactured according to the following general procedure:

Preparation of the Ointment:

1. All dry excipient ingredients are assembled and weighed out according to the formula in Table 2 and placed in an appropriate vessel. Hereinafter, an excipient is an inert substance which is added to the free base form of the nitrogen mustard or its pharmaceutically acceptable HX salt to provide bulk. Hereinafter, the dry excipient ingredients are indicated as being added as solid weight, such as gram, i.e. gm.

2. Particle sizes of the dry material are reduced to a uniform size through tritration.
3. Polypropylene glycol (PPG), propylene glycol (PG), polyethylene glycol (PEG) or ethylene glycol (EG) from about 15 to about 60 percent by weight is then added via the principle of geometric dilution to form a smooth paste. Once a smooth paste is achieved, the propylene or ethylene glycol continues to be added until a volume that retains a flow like quality is obtained.
4. The entire contents are then transferred to a large beaker. A spin bar is added and the beaker is placed on a magnetic stirring plate and mixing is begun.
5. As the mixture continues to spin, glycerin is added. While the mixture spins, the original vessel is washed with from about 15 to about 60 percent by weight ethoxy diglycol and the contents of the vessel are added to the spinning mixture in the beaker.
6. After the 2-(2-ethoxyethoxy)ethanol is added, kris-ester is added to the spinning mixture. This mixture then is spun for approximately one to two hours. After the spinning is finished the mixture is covered and left to sit over-night.
7. The next day the mixture is mixed with a high shear mixer to a uniform consistency with minimal to no air. Air and moisture may be removed during mixing by applying a vacuum from about 0.01 to about 0.1 torr. The mixture is then brought to ambient pressure by adding dry nitrogen.

Adding the Nitrogen Mustard:

8. The appropriate concentration and amount of Nitrogen mustard is reconstituted with absolute alcohol (200 proof) then added to the appropriate amount of non-aqueous vehicle or carrier, wherein the non-aqueous vehicle or carrier does not include petrolatum or ethanol and mixed to a uniform consistency via agitation for 60-90 seconds For example, in an embodiment, a concentration in mg/ml of the pharmaceutically acceptable Nitrogen Mustard.HCl in the non-aqueous vehicle or carrier that does not include petrolatum or ethanol is advantageously from about 1 mg of Nitrogen Mustard.HCl per 100 ml of non-aqueous vehicle to about 2000 mg of Nitrogen Mustard.HCl per 100 ml of non-aqueous vehicle. In an embodiment, a concentration in mg/ml of Nitrogen Mustard.HCl in a non-aqueous vehicle or carrier that does not include petrolatum or ethanol is advantageously from about 10 mg of Nitrogen Mustard.HCl per 100 ml of non-aqueous vehicle or carrier that does not include petrolatum or ethanol to about 40 mg of Nitrogen Mustard.HCl per 100 ml of non-aqueous vehicle or carrier that does not include petrolatum or ethanol. In an embodiment, a concentration in mg/ml of Nitrogen Mustard.HCl used in a non-aqueous vehicle or carrier that does not include petrolatum or ethanol is advantageously from about 15 mg of Nitrogen Mustard.HCl per 100 ml of non-aqueous vehicle or carrier that does not include petrolatum or ethanol to about 30 mg of Nitrogen Mustard.HCl per 100 ml of non-aqueous vehicle or carrier that does not include petrolatum or ethanol.
9. This mixture is then poured into a 50 ml flip top plastic cylinder and shipped to the appropriate patient.

Clean-Up:

10. All vessels used in the process are placed in a Sodium Thiosulfate-Sodium Bicarbonate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

Example 2

Preparation of a Topical Ointment Comprising Bis-(2-chloroethyl)methylamine Hydrochloride in a Pharmaceutically Acceptable Vehicle or Carrier (a) Composition of the Topical Ointment
The components/composition of the topical ointment is provided in the following Table 3.

TABLE 3

Composition B

| Ingredient[a] | Parts per 100 Parts by Weight of a Topical Ointment |
|---|---|
| Dimethicone or Cyclomethicone | 10-60 |
| 2-(2-ethoxyethoxy)ethanol | 10-16 |
| Hydroxypropylcellulose, NF (1500 cps) | 0-15 |
| Menthol crystals, USP | 0-1 |
| Butylated hydroxytoluene, NF (BHT) | 0-1 |
| Glycerin, USP | 1-2 |
| Edetate disodium, USP | 0-0.05 |
| Decyl methyl sulfoxide | 0-0.125 |
| Kris-Ester 236 liquid | 0-5 |
| Anhydrous secondary or tertiary alcohol | 1-20 |
| Bis-(2-chloroethyl)methylamine HCl[b] | 0.001-2.0 |
| $C_nH_{(2n+2)}COOH$, (n = 1-6) | 0.01-15 |

[a]Slight overages of the ingredients may be used as required to offset losses during manufacture.
[b]Available from Merck & Co., West Point, PA 19486

(b) Manufacturing
The topical ointment may be manufactured according to the following general procedure:
Preparation of the Dimethicone or Cyclodimethicone Ointment:
1. All dry excipient ingredients are assembled and weighed out according to the formula in Table 3 and placed in an appropriate vessel.
2. Particle sizes of the dry material are reduced to a uniform size through tritration.
3. Dimethicone or cyclomethicone from about 10 to about 60 percent by weight is then added via the principle of geometric dilution to form a smooth paste. Once a smooth paste is achieved, the Dimethicone or cyclomethicone continues to be added until a volume that retains a flow like quality is obtained.
4. The entire contents are then transferred to a large beaker. A spin bar is added and the beaker is placed on a magnetic stiffing plate and mixing is begun.
5. As the mixture continues to spin, glycerin is added. While the mixture spins, the original vessel is washed with from about 10 to about 16 percent by weight 2-(2-ethoxyethoxy)ethanol and the contents of the vessel are added to the spinning mixture in the beaker.
6. After the 2-(2-ethoxyethoxy)ethanol is added, from about 0.01-15 percent by weight of a pH modifier such as citric acid, lactic acid or aliphatic acids having a formula $C_nH_{(2n+2)}COOH$, (n=1-6) is added to the spinning mixture. This mixture then is spun for approximately one to two hours. After the spinning is finished the mixture is covered and left to sit over-night.

7. The next day the mixture is mixed with a high shear mixer to a uniform consistency with minimal to no air. Air and moisture may be removed during mixing by applying a vacuum from about 0.01 to about 0.1 torr. The mixture is then brought to ambient pressure by adding dry nitrogen.

Combining the Nitrogen Mustard and the Dimethicone or Cyclodimethicone Non-Aqueous Vehicle or Carrier that does not include petrolatum or ethanol of step 7) above:

The nitrogen mustard and the dimethicone or cyclodimethicone non-aqueous vehicle or carrier may be combined by agitating for 60-90 seconds using a high shear mixer to mix 1) an appropriate amount of nitrogen mustard having been be reconstituted with an secondary or tertiary alcohol such as isopropyl alcohol, wherein ethanol has been rigorously excluded from the secondary or tertiary alcohol such as isopropyl alcohol, and 2) the appropriate amount of non-aqueous vehicle or carrier from step 7), supra. For example, in an embodiment, a concentration in mg/ml of the pharmaceutically acceptable Nitrogen Mustard.HCl in the non-aqueous vehicle or carrier is advantageously from about 1 mg of Nitrogen Mustard.HCl per 100 ml of non-aqueous vehicle to about 2000 mg of Nitrogen Mustard.HCl per 100 ml of non-aqueous vehicle. In another embodiment, a concentration in mg/ml of the pharmaceutically acceptable Nitrogen Mustard.HCl used in the non-aqueous vehicle or carrier is advantageously from about 10 mg of Nitrogen Mustard.HCl per 100 ml of non-aqueous vehicle or carrier to about 40 mg of Nitrogen Mustard.HCl per 100 ml of non-aqueous vehicle or carrier. In another embodiment, a concentration in mg/ml of the pharmaceutically acceptable Nitrogen Mustard.HCl used in the non-aqueous vehicle or carrier is advantageously from about 15 mg of Nitrogen Mustard.HCl per 100 ml of non-aqueous vehicle or carrier to about 30 mg of Nitrogen Mustard.HCl per 100 ml of non-aqueous vehicle or carrier.

This mixture is then poured into a 50 ml flip top plastic cylinder and shipped to the appropriate patient. The mixture advantageously has an essentially completely uniform consistency.

Clean-Up:

All vessels used in the process are placed in a 5% w/v sodium bicarbonate-sodium thiosulfate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

Example 3

Preparation of a Topical Ointment Comprising Bis-(2-chloroethyl)methylamine Hydrochloride in a Pharmaceutically Acceptable Vehicle or Carrier The topical ointment described in Example 1 or 2 may alternatively be manufactured according to the following general procedure:

Preparation of the Ointment:

1. All dry (i.e., solid) excipient ingredients, except for hydroxypropylcellulose, are assembled and weighed out according to the formula in Table 2 or 3 and placed in appropriate containers.
2. All wet (i.e., liquid) excipient ingredients, except for glycerin and 2-(2-ethoxyethoxy)ethanol, are weighed out according to the formula in Table 2 or 3 and combined in a large vessel with all dry excipient ingredients. These excipient ingredients are mixed at low speed to form a uniform mixture ("Excipient Mixture").
3. In a separate vessel, Glycerin and Hydroxypropyl cellulose are weighed out according to the formula in Table 2 or 3, combined in the vessel and mixed at low speed to form a uniform suspension ("Glycerin/HPC suspension").
4. While maintaining constant low speed mixing, the Glycerin/HPC suspension is added directly to the Excipient Mixture in the large vessel to form a uniform ointment (or gel) base ("Ointment base").

Adding the Nitrogen Mustard:

5. The appropriate concentration and amount of Nitrogen Mustard is reconstituted with 2-(2-ethoxyethoxy)ethanol and added to the Ointment base. A final uniform Nitrogen Mustard product ointment is obtained by applying low speed constant mixing. Nitrogen Mustard product ointment is filled in appropriate size aluminum tube containers, crimp sealed to close and complete.

Example 4

Effect of Alcohol on Stability of Nitrogen Mustard Ointment Compositions

Two compositions of nitrogen mustard ointment (Compositions C and D) were produced to assess the differences in alcohols used for diluting the nitrogen mustard. Samples were tested at various temperature conditions (5, 25 and 40° C.) and assessed for stability with use of an HPLC assay. The formulations for Compositions C and D are encompassed by those described in Tables 4 and 5 below.

TABLE 4

Composition C

| Component | Percent by weight of the composition |
| --- | --- |
| MUSTARGEN ® (mechlorethamine hydrochloride and sodium chloride) | 0.001-5% |
| Hydroxypropyl cellulose, MXF | 0.01-5% |
| Edetate disodium dihydrate, USP | 0.01-1% |
| Menthol, USP | 0.01-1% |
| Butylated hydroxytoluene, USP | 0.01-10% |
| 2-(2-ethoxyethoxy) ethanol (pharmaceutical grade) | 1-99% |
| Absolute alcohol (ethanol), USP | 1-50% |
| Propylene glycol, USP | 1-50% |
| Glycerin, USP | 1-50% |
| Citric acid, USP | 1-25% |
| Total | 100% |

TABLE 5

Composition D

| Component | Quality Standard | Percent by weight of the composition |
| --- | --- | --- |
| Mechlorethamine hydrochloride | USP | 0.001-5% |
| Hydroxypropyl cellulose | NF | 0.01-5% |
| Edetate disodium (dihydrate) | USP | 0.01-1% |
| (DL) Menthol | USP | 0.01-1% |
| Butylated hydroxytoluene | NF | 0.01-10% |
| 2-(2-ethoxyethoxy)ethanol | NF | 1-99% |
| Isopropyl alcohol | USP | 1-50% |

TABLE 5-continued

Composition D

| Component | Quality Standard | Percent by weight of the composition |
|---|---|---|
| Propylene glycol | USP | 1-50% |
| Glycerin | USP | 1-50% |
| Lactic acid (racemic) | USP | 1-25% |
| Sodium chloride | USP | 0.01-10% |
| Total | | 100% |

Composition C (~15% absolute alcohol) yielded the following results when tested for stability at 1, 2 and 3 weeks post production (See Table 6).

TABLE 6

Label Strength of Composition C over time stored at various temperatures in aluminum foil tubes.

| Day of assessment | Storage Temperature | % MCHCl (or label strength) |
|---|---|---|
| 7 | 5° C. | 96.36 |
| | 25° C. | 81.37 |
| | 40° C. | 20.50 |
| 14 | 5° C. | 92.54 |
| | 25° C. | 68.44 |
| | 40° C. | 1.26 |
| 21 | 5° C. | 92.83 |
| | 25° C. | 58.85 |
| | 40° C. | −2.22 |

Composition D (~15% isopropanol) yielded the following results when tested for stability at 10, 15, and 20 days post production (See Table 7).

TABLE 7

Label Strength of Composition D over time stored at various temperatures in aluminum foil tubes.

| Day of assessment | Storage Temperature | % MCHCl (or label strength) |
|---|---|---|
| 10 | 5° C. | 99.54 |
| | 25° C. | 98.42 |
| | 40° C. | 79.25 |
| 15 | 5° C. | 99.11 |
| | 25° C. | 95.75 |
| | 40° C. | 72.91 |
| 20 | 5° C. | 96.89 |
| | 25° C. | 93.07 |
| | 40° C. | 67.48 |

According to the data in Tables 6 and 7, absolute alcohol (ethanol) caused significant degradation of the mechlorethamine hydrochloride, while isopropyl alcohol did not.

After 18 months of storage at ambient temperature, i.e., between about 20° C. and 25° C., about 80% or more of the mechlorethamine hydrochloride remained in Composition D (in other words, there was about 20% or less loss of mechlorethamine hydrochloride due to degradation in Composition D).

Example 5

Effect of pH on Stability of Nitrogen Mustard Ointment Compositions

Mechlorethamine hydrochloride was dissolved in water, pH 5 buffer, and pH 7 buffer, and the degradation of the mechlorethamine hydrochloride was measured over a period of about 28 hours. The results are shown in FIG. 6.

Figure 6:
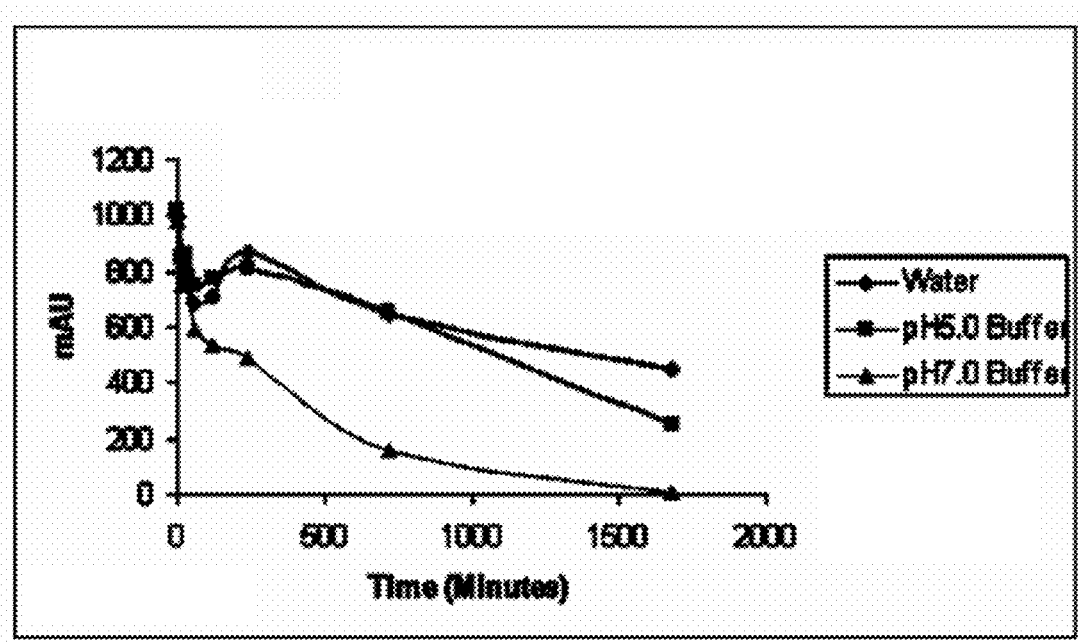
FIG. 6 depicts rate of MCHCl decomposition vs pH, in accordance with embodiments of the present invention.

As illustrated in FIG. 6, the mechlorethamine hydrochloride decomposes much faster in pH 7 buffer than in water (pH ~5.2) or pH 5 buffer. The half life of the mechlorethamine hydrochloride in pH 7 buffer is about 2 hours, and the mechlorethamine hydrochloride decomposes totally after 28 hours. Thus, one can conclude that mechlorethamine hydrochloride decomposes faster in higher pH solutions, and that the presence of inorganic salts (such as in the pH 7 buffer) also can accelerate decomposition.

Example 6

Preparation of a Representative Dispersion

Mechlorethamine HCl (MCHCl) is readily dispersed in 2-(2-ethoxyethoxy)ethanol by depositing dry MCHCl powder into a suitable container, such as a flask, a vial or a bottle, adding 2-(2-ethoxyethoxy)ethanol, and dispersing the MCHCl by mixing, such as by stirring, sonicating or shaking.

Accordingly, a 0.5 w/w solution of MCHCl dissolved in 2-(2-ethoxyethoxy)ethanol is readily prepared by placing 25 mg of MCHCl powder in a 25 mL glass vial, adding 4.975 grams of 2-(2-ethoxyethoxy)ethanol, and stirring gently for 1 hour.

Equilibrium solubility experiments revealed that the solubility of MCHCl in 2-(2-ethoxyethoxy)ethanol is approximately 1.6% w/w.

Example 7

Stability of mechlorethamine HCl Dispersed in 2-(2-ethoxyethoxy)ethanol at Various Temperatures 0.5% w/w solutions of mechlorethamine HCl (MCHCl) dissolved in 2-(2-ethoxyethoxy)ethanol (composition E); 2-(2-ethoxyethoxy)ethanol and NaCl (composition F); 2-(2-ethoxyethoxy)ethanol and 85% aqueous lactic acid (composition G); and 2-(2-ethoxyethoxy)ethanol, NaCl, and 85% aqueous lactic acid (composition H) were prepared, and aliquot parts were stored at various temperatures in glass vials sealed from the atmosphere. Percent MCHCl in each sample was measured by HPLC with a MS detector over time.

HPLC-MS was performed using the following parameters:

TABLE 8

High Performance Liquid Chromatography (HPLC) Parameters

| | |
|---|---|
| Device: | Waters ® Alliance 2695 Separation Module |
| Column: | Symmetry ® MS C18 column, 3.5 µ, 150 × 2.1 mm |
| Flow rate: | 0.2 mL/minute |
| Run time: | 60 minutes |
| Retention time: | ~17 minutes |
| Detector: | MS |
| Mobile phase: | A: 0.1% formic acid in water |
| | B: 0.1% formic acid in acetonitrile:water (95:5) |

TABLE 8-continued

High Performance Liquid Chromatography (HPLC) Parameters

|  | Time (minutes) | % A | % B |
|---|---|---|---|
| Gradient: | 0 | 99% | 1% |
|  | 3.10 | 1% | 99% |
|  | 22 | 1% | 99% |
|  | 41 | 99% | 1% |
|  | 50 | 99% | 1% |
|  | 60 | 99% | 1% |

TABLE 9

Mass Spectrometry (MS) Parameters

| Device: | Waters ® Micromass ESCi multimode ionization |
|---|---|
| Capillary: | 2.60 kV |
| Cone: | 21.0 V |
| Extractor: | 3 V |
| Rf Lens: | 0 V |
| Temperature: | Source temperature: 120° C. |
|  | Desolvation temperature: 350° C. |
| Gas Flow: | Desolvation: 400 L/hour |
|  | Cone: 50 L/hour |

Samples were prepared for HPLC analysis as follows: A nitrogen mustard sample (100 μL) was removed from the stored glass vials, combined with a 150 mM NaCl solution (100 μL), and mixed. The resulting solution was then combined with 750 mL of a solution of sodium diethyldithiocarbamate (DDTC) in sodium hydroxide (10 mg/mL of DDTC in 0.1M NaOH), mixed, and then incubated at 37° C. for 30 minutes. The resulting solution was then allowed to cool to room temperature and extracted three times with 1000 μL ethyl acetate. The combined organic extracts were evaporated to dryness under nitrogen at room temperature to form a residue. The residue was then reconstituted with 1000 μL of acetonitrile:water (20:80) with 0.1% v/v formic acid.

The results of the stability studies are presented in Tables 10 and 11 below.

TABLE 10

Stability of MCHCl compositions containing 2-(2-ethoxyethoxy) ethanol stored at room temperature Percent nitrogen mustard (MCHCl) remaining in samples stored at ~25° C. (mean ± SD)

| Time (Weeks) | Composition E | Composition F | Composition G | Composition H |
|---|---|---|---|---|
| 0 | 102.31 ± 0.71 | 100.43 ± 0.29 | 98.40 ± 1.58 | 102.61 ± 0.53 |
| 1 | 97.31 ± 0.38 | 99.05 ± 0.24 | 103.68 ± 0.14 | 101.11 ± 0.15 |
| 2 | 102.94 ± 1.21 | 99.39 ± 0.52 | 103.57 ± 0.19 | 104.72 ± 0.07 |
| 3 | 97.43 ± 0.06 | 97.38 ± 0.04 | 95.25 ± 0.11 | 103.96 ± 0.41 |
| 4 | 103 ± 2.65 | 100.79 ± 0.37 | 100.55 ± 0.10 | 101.33 ± 0.10 |
| 5 | 99.59 ± 0.05 | 97.23 ± 0.31 | 99.98 ± 0.06 | 104.65 ± 0.27 |
| 6 | 100.03 ± 0.87 | 97.11 ± 2.56 | 97.08 ± 1.87 | 100.75 ± 5.38 |
| 7 | 100.15 ± 5.56 | 96.19 ± 2.75 | 96.74 ± 1.58 | 99.07 ± 3.98 |
| 8 | 98.68 ± 5.04 | 92.18 ± 1.45 | 95.49 ± 3.46 | 96.09 ± 3.65 |

Composition E: 0.5% MCHCl; 99.5% 2-(2-ethoxyethoxy) ethanol
Composition F: 0.5% MCHCl; 0.18% w/w NaCl; 99.32% 2-(2-ethoxyethoxy) ethanol
Composition G: 0.5% MCHCl; 3.65% w/w 85% aqueous lactic acid; 95.85% 2-(2-ethoxyethoxy) ethanol
Composition H: 0.5% MCHCl; 0.18% w/w NaCl; 3.65% w/w 85% aqueous lactic acid; 95.67% 2-(2-ethoxyethoxy) ethanol Table 10 reveals that the inclusion of the stabilizing agents sodium chloride, lactic acid or both do not affect MCHCl stability in 2-(2-ethoxyethoxy)ethanol. Therefore, it can be concluded from Table 10 that MCHCl is stable in 2-(2-ethoxyethoxy)ethanol at room temperature for up to 8 weeks without the need for stabilizing agents, such as sodium chloride, lactic acid, or a combination thereof. Further, Table 10 illustrates that MCHCl is stable in 2-(2-ethoxyethoxy)ethanol at room temperature for up to 8 weeks without the addition of any antioxidant, such as BHT, EDTA, benzyl alcohol, or a paraben, as none of Compositions E to H contain an antioxidant. Further still, Table 10 illustrates that MCHCl is stable in 2-(2-ethoxyethoxy)ethanol at room temperature for up to 8 weeks, even in the presence of 0.5% by weight water, which is included in Compositions G and H in the form of aqueous lactic acid. Therefore, 2-(2-ethoxyethoxy)ethanol would serve as a useful formulation aid.

TABLE 11

Stability of MCHCl compositions containing 2-(2-ethoxyethoxy) ethanol stored at elevated temperatures Percent MCHCl remaining in samples of Composition E (mean ± SD)

| Time (Days) | Storage at 60° C. | Storage at 80° C. |
|---|---|---|
| 0 | 100.76 ± 0.91 | 103.13 ± 0.86 |
| 1 | 99.63 ± 3.66 | 97.20 ± 6.38 |
| 2 | 98.79 ± 2.03 | 95.85 ± 3.45 |
| 3 | 96.90 ± 4.9 | 92.98 ± 1.32 |
| Time (Weeks) |  |  |
| 1 | 92.04 ± 4.06 | 90.66 ± 4.80 |
| 2 | 78.99 ± 0.99 | 75.73 ± 2.96 |
| 3 | 73.44 ± 4.91 | 65.36 ± 5.51 |
| 4 | 67.99 ± 3.96 | 58.94 ± 4.96 |

Table 11 reveals that, even at elevated temperatures, MCHCl remains stable in 2-(2-ethoxyethoxy)ethanol for significant periods of time, even at temperatures as high as 80 degrees Celsius for 1 week. This further underscores the utility and versatility of the unexpected observation that 2-(2-ethoxyethoxy)ethanol is a useful formulation aid for facilitating the storage, transport and dispensing of such alkylating agents in dispersion.

Example 8

Stability of Nitrogen Mustard Ointment Batches after Storage at Room Temperature Three batches of ointment having 0.02% w/w mechlorethamine HCl according to Composition D above were prepared and stored in aluminum foil tubes at 25° C. and 60% relative humidity. Percent MCHCl in each sample was measured by HPLC over a period of 6 months.

HPLC was performed using the following parameters:

TABLE 12

| HPLC Parameters | | | |
|---|---|---|---|
| Column: | Alltech Apollo C18, 5 µm, 4.6 × 250 mm or equivalent | | |
| Flow rate: | 1.2 mL/minute | | |
| Run time: | 22 minutes | | |
| Column temperature: | 45° C. | | |
| Autosampler temperature: | Ambient | | |
| Injection volume. | 5 µL | | |
| Detector: | Ultraviolet detector at 276 nm | | |
| Mobile phase: | A: 5 mM $H_3PO_4$ in $H_2O$, pH adjusted to 3 with triethylamine B: Acetonitrile | | |
| | Time (minutes) | % A | % B |
| Gradient: | 0 | 70 | 30 |
| | 2 | 70 | 30 |
| | 8 | 10 | 90 |
| | 12 | 0 | 100 |
| | 12.5 | 0 | 100 |
| | 14 | 70 | 30 |
| | 22 | 70 | 30 |

Samples were prepared for HPLC analysis as follows: A nitrogen mustard sample (25 mg) was removed from the aluminum foil tube, combined with a 150 mM NaCl solution (0.5 mL), and mixed. The resulting solution was then combined with a 10% solution of DDTC in sodium hydroxide (100 µL), mixed, and then incubated at 37° C. for 30 minutes. The resulting solution was then allowed to cool to room temperature and extracted three times with 1.0 mL ethyl acetate. The combined organic extracts were then dried over anhydrous $K_2CO_3$, the $K_2CO_3$ was filtered, and the filtrate was evaporated to dryness to form a residue. The residue was then reconstituted with 1.0 mL of acetonitrile and filtered through a 0.2 µm nylon syringe filter.

The results are summarized in Tables 13, 14, and 15 below.

TABLE 13

Results for 0.02% Ointment Batch 1

| Time (mos.) | Average % of Label Concentration (by HPLC assay) |
|---|---|
| 0 | 99.6% |
| 1 | 99.2% |
| 2 | 95.2% |
| 3 | 86.1% |
| 4 | 76.2% |
| 5 | 70.5% |
| 6 | 65.6% |
| 7 | 61.2% |

*Averages were taken from 3 to 6 samples.

As illustrated by the data, at least about 85% of the MCHCl is present in 0.02% ointment batch 1 after storage for up to about 3 months; and at least about 65% of the MCHCl is present in 0.02% ointment batch 1 after storage for up to about 6 months.

TABLE 14

Results for 0.02% Ointment Batch 2

| Time (mos.) | Average % of Label Concentration (by HPLC assay) |
|---|---|
| 0 | 102.8% |
| 2 | 89.7% |

*Averages were taken from 3 to 6 samples.

As illustrated by the data, at least about 85% of the MCHCl is present in 0.02% ointment batch 2 after storage for up to about 2 months.

TABLE 15

Results for 0.02% Ointment Batch 3

| Time (mos.) | Average % of Label Concentration (by HPLC assay) |
|---|---|
| 0 | 102.9% |
| 2 | 89.4% |

*Averages were taken from 3 to 6 samples.

As illustrated by the data, at least about 85% of the MCHCl is present in 0.02% ointment batch 3 after storage for up to about 2 months.

Figure 7:
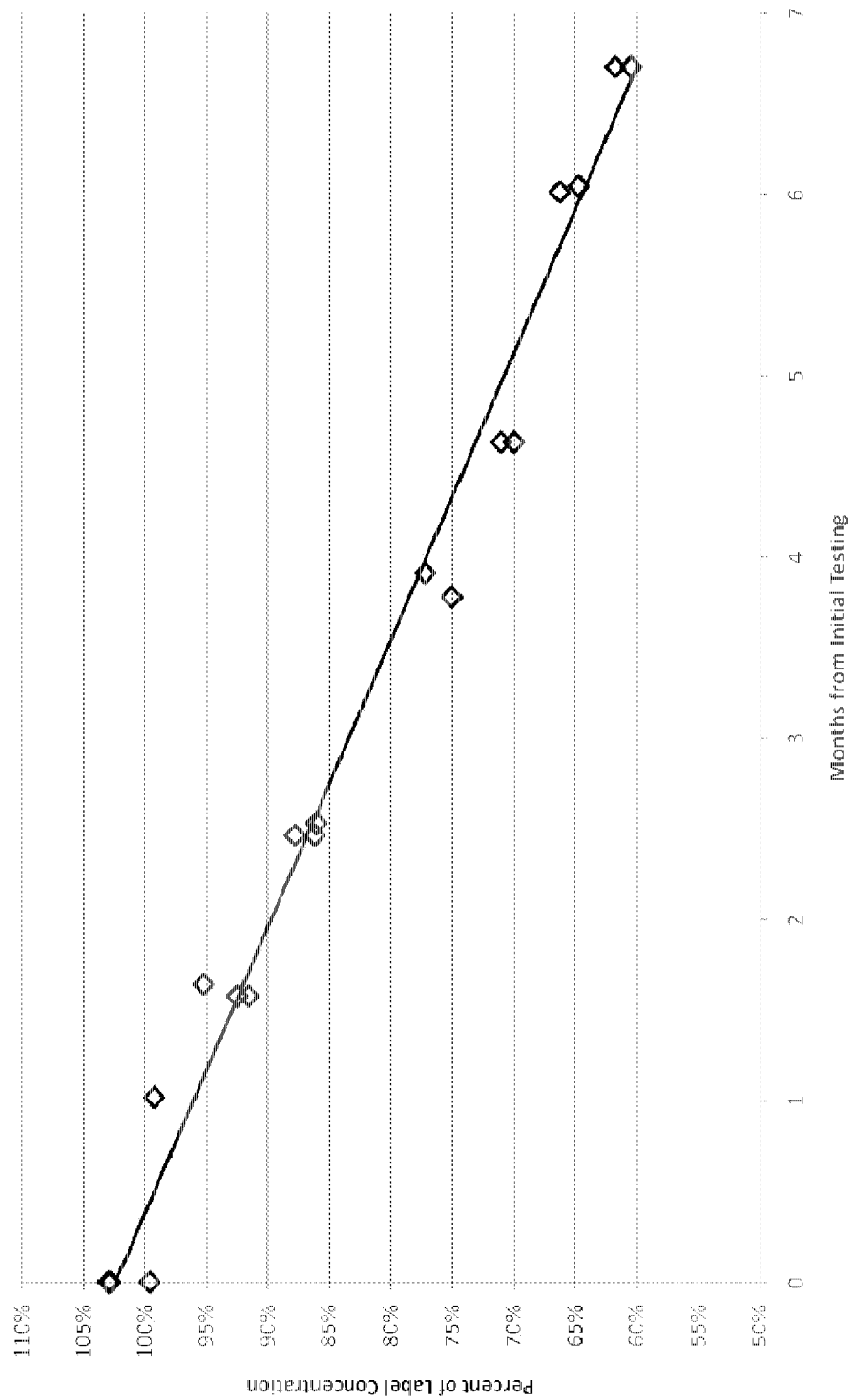
FIG. 7 depicts the results of stability testing on MCHCl 0.02% ointment batches at 25° C., as described in Example 8.

The results for 0.02% ointment batches 1, 2, and 3 stored at 25° C. and 60% relative humidity are also illustrated in FIG. 7.

Example 9

Stability of 0.02% w/w Nitrogen Mustard Ointment Batches after Storage under Refrigeration Several batches of ointment having 0.02% w/w mechlorethamine HCl were prepared according to Composition D above and stored in aluminum foil tubes under refrigeration (2° C. to 8° C.). Percent MCHCl in each batch was measured by HPLC over time using the HPLC method described in Example 8. The results are summarized in Tables 16 to 19 below.

TABLE 16

Results for 0.02% Ointment Batch 1

| Time (mos.) | Average % of Label Concentration (by HPLC assay) |
|---|---|
| 0 | 101.9% |
| 6 | 102.2% |
| 12 | 97.0% |
| 25 | 97.5% |
| 31 | 95.4% |

*Averages were taken from 3 samples.

As illustrated by the data, at least about 95% of the MCHCl is present in 0.02% ointment batch 1 after storage for up to about 12 months, 25 months, or 31 months.

TABLE 17

Results for 0.02% Ointment Batch 2

| Time (mos.) | Average % of Label Concentration (by HPLC assay) |
|---|---|
| 0 | 103.7% |
| 4 | 103.1% |
| 7 | 107.0% |
| 9 | 104.3% |
| 12 | 94.3% |
| 19 | 98.7% |
| 24 | 97.7% |

*Averages were taken from 3 to 6 samples.

As illustrated by the data, at least about 90% of the MCHCl is present in 0.02% ointment batch 2 after storage for up to about 12 months, 19 months, or 24 months.

TABLE 18

Results for 0.02% Ointment Batch 3

| Time (mos.) | Average % of Label Concentration (by HPLC assay) |
|---|---|
| 0 | 107.5% |
| 3 | 99.5% |
| 7 | 101.3% |
| 9 | 97.6% |
| 12 | 95.8% |
| 18 | 97.7% |

*Averages were taken from 3 samples.

As illustrated by the data, at least about 95% of the MCHCl is present in 0.02% ointment batch 3 after storage for up to about 7 months, 12 months, or 18 months.

TABLE 19

Results for 0.02% Ointment Batch 4

| Time (mos.) | Average % of Label Concentration (by HPLC assay) |
|---|---|
| 0 | 100.1% |
| 5 | 102.9% |
| 6 | 101.9% |

*Averages were taken from 3 samples.

As illustrated by the data, at least about 95% of the MCHCl is present in 0.02% ointment batch 4 after storage for up to about 6 months.

Figure 8:
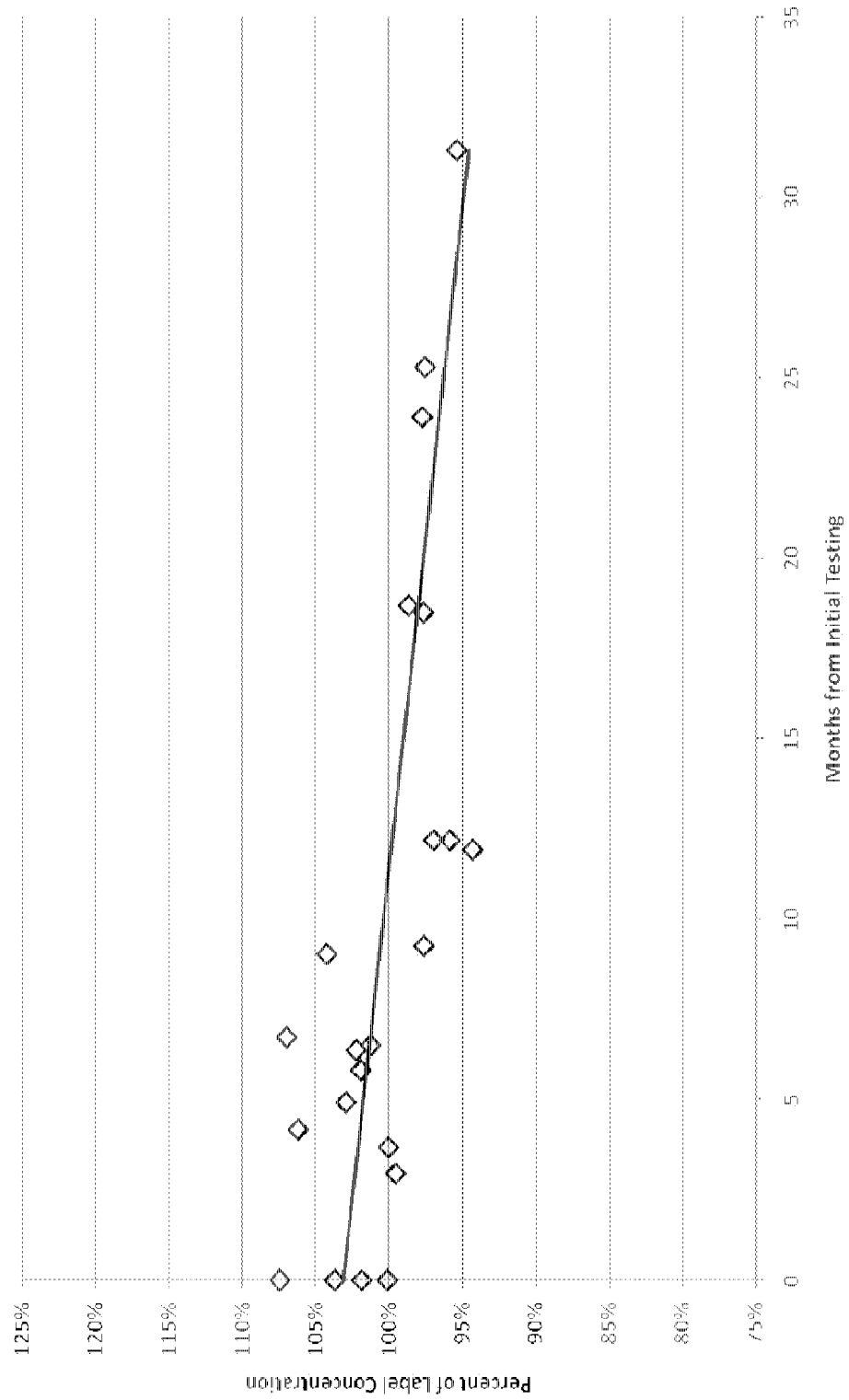
FIG. 8 depicts the results of stability testing on MCHCl 0.02% ointment batches at 2-8° C., as described in Example 9.

The results for 0.02% ointment batches 1, 2, 3, and 4 stored at 2-8° C. are also illustrated in FIG. 8.

Example 10

Stability of 0.04% w/w Nitrogen Mustard Ointment Samples after Storage under Refrigeration Several batches of ointment having 0.04% w/w mechlorethamine HCl were prepared according to Composition D above and stored in aluminum foil tubes under refrigeration (2° C. to 8° C.). Percent MCHCl in each batch was measured by HPLC over time using the HPLC method described in Example 8. The results are summarized in Tables 20 to 22 below.

TABLE 20

Results for 0.04% Ointment Batch 1

| Time (mos.) | Average % of Label Concentration (by HPLC assay) |
|---|---|
| 0 | 116.4% |
| 2 | 93.7% |
| 3 | 86.4% |
| 5 | 105.2% |
| 6 | 103.3% |
| 7 | 107.7% |
| 8 | 106.7% |
| 9 | 104.0% |
| 10 | 94.9% |
| 12 | 102.8% |
| 15 | 98.8% |
| 18 | 98.5% |
| 24 | 92.9% |

*Averages were taken from 3 to 9 samples.

As illustrated by the data, at least about 90% of the MCHCl is present in 0.04% ointment batch 1 after storage for up to about 6 months, 12 months, or 24 months.

TABLE 21

Results for 0.04% Ointment Batch 2

| Time (mos.) | Average % of Label Concentration (by HPLC assay) |
|---|---|
| 0 | 105.5% |
| 2 | 110.9% |
| 5 | 98.7% |
| 8 | 97.0% |
| 11 | 97.2% |
| 14 | 98.7% |
| 17 | 97.0% |
| 23 | 95.5% |

*Averages were taken from 3 to 6 samples.

As illustrated by the data, at least about 95% of the MCHCl is present in 0.04% ointment batch 2 after storage for up to about 5 months, 11 months, 17 months, or 23 months.

TABLE 22

Results for 0.04% Ointment Batch 3

| Time (mos.) | Average % of Label Concentration (by HPLC assay) |
|---|---|
| 0 | 101.6% |
| 3 | 99.0% |
| 6 | 97.9% |
| 9 | 99.9% |
| 12 | 98.0% |
| 15 | 98.1% |
| 18 | 98.9% |

*Averages were taken from 3 samples.

As illustrated by the data, at least about 98% of the MCHCl is present in 0.04% ointment batch 3 after storage for up to about 6 months, 9 months, 12 months, 15 months, or 18 months.

Figure 9:
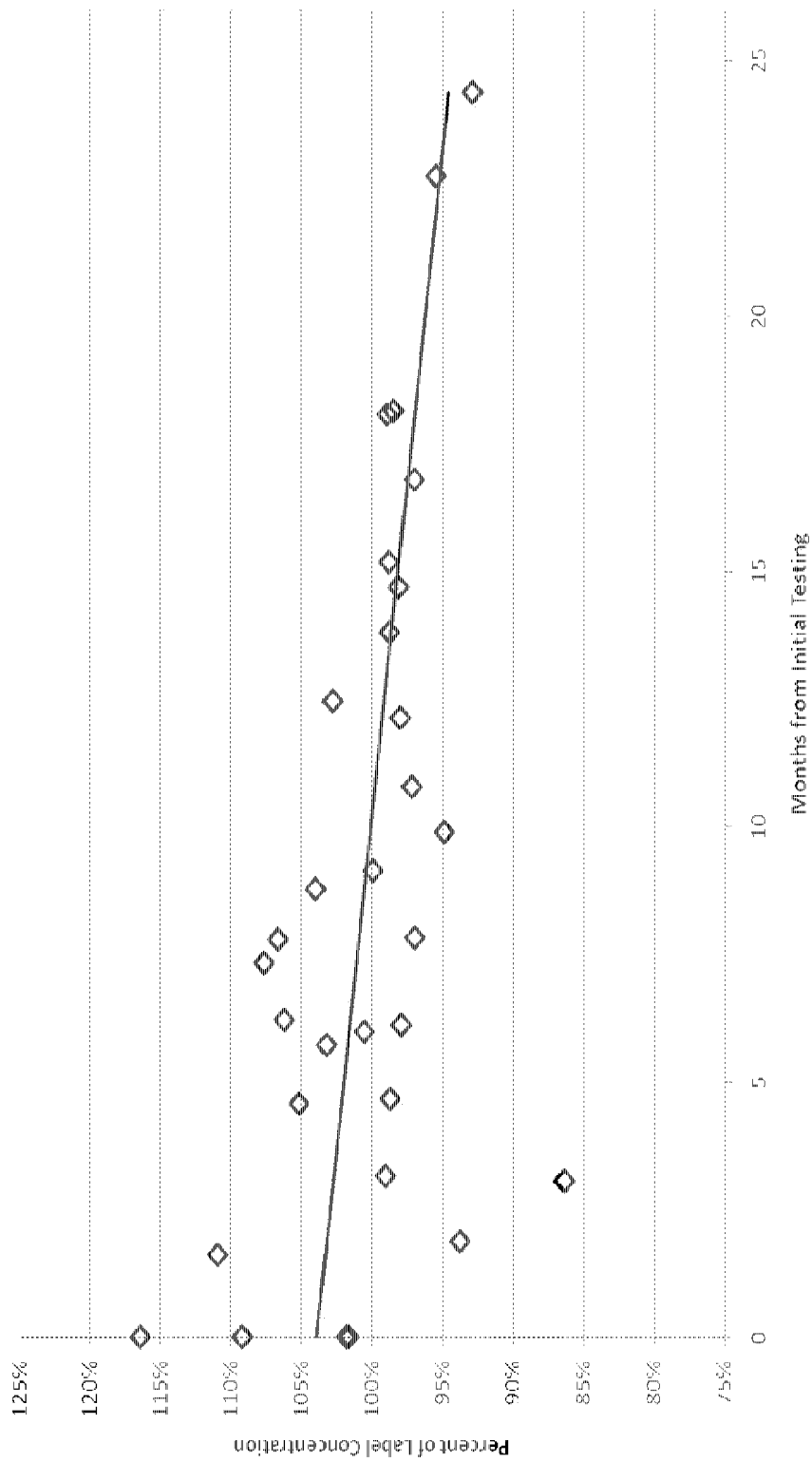
FIG. 9 depicts the results of stability testing on MCHCl 0.04% ointment batches at 2-8° C., as described in Example 10.

The results for 0.02% ointment batches 1, 2, and 3 stored at 2-8° C. are also illustrated in FIG. 9.

Example 11

Identifying and Quantifying Degradation Products in MCHCl Ointments

Three batches of ointment having 0.02% w/w mechlorethamine HCl were prepared according to Composition D above and stored in screw cap ointment tubes under refrigeration (2° C. to 8° C.) for various lengths of time. Batch 1 was stored for 6 months, Batch 2 was stored for 13 months, and Batch 3 was stored for 22 months. The presence of the nitrogen mustard degradation products in each batch was determined by HPLC-MS, and compared to that of placebo (ointment without mechlorethamine HCl).

HPLC-MS was performed using the following parameters:

TABLE 23

| HPLC-MS Parameters | |
|---|---|
| Device: | Agilent HP1100 HPLC system equipped with diode array detector |
| | Micromass QTOF-API US mass spectromater MassLynx 4.0 with SP 4 |
| | Micromass QTOF-Ultima mass spectromater MassLynx 4.0 with SP 4 |
| Column: | Water Symmetry ® C18 column, 3.5μ, 100 Å, 150 × 2.1 mm |
| Column Temp.: | 25° C. |

TABLE 23-continued

| HPLC-MS Parameters | | | |
|---|---|---|---|
| Flow rate: | 0.2 mL/minute | | |
| Run time: | 60 minutes | | |
| Cone voltage: | 35 V, 75 V | | |
| Mobile phase: | A: 0.1% formic acid in water | | |
| | B: 0.1% formic acid in acetonitrile: water (95:5) | | |
| | Time (minutes) | % A | % B |
| Gradient: | 0 | 99% | 1% |
| | 3.10 | 1% | 99% |
| | 22 | 1% | 99% |
| | 41 | 99% | 1% |
| | 50 | 99% | 1% |
| | 60 | 99% | 1% |

MCHCl was found to have a m/z value of 156.0347. The calculated m/z values for several proposed nitrogen mustard degradation products that may be formed from nucleophiles present in Composition D or in the environment (e.g., water) are shown in Table 24 below.

TABLE 24

| Nucleophile | Proposed Nitrogen Mustard Degradation Product | Calculated m/z value |
|---|---|---|
| Water | $H_3C-N(CH_2CH_2Cl)-CH_2CH_2-OH$ (DP-1) | 138.0697 |
| | $H_3C-N(CH_2CH_2-OH)-CH_2CH_2-OH$ (DP-2) | 119.6243 |
| Edetate disodium | (DP-3) | 457.8 |
| | (DP-4) | 758.55 |

TABLE 24-continued

| Nucleophile | Proposed Nitrogen Mustard Degradation Product | Calculated m/z value |
|---|---|---|
| Glycerin | (DP-5) structure: H₃C—N(CH₂CH₂Cl)—CH₂CH₂—O—CH₂—CH(OH)—CH₂OH  or  H₃C—N(CH₂CH₂Cl)—CH₂CH₂—O—CH(CH₂OH)(CH₂OH) | 213.69 |
|  | (DP-6) three isomeric structures shown, each containing H₃C—N(CH₂CH₂—O—glyceryl)—CH₂CH₂—O—glyceryl connectivity | 270.33 |
| Isopropyl alcohol | (DP-7) H₃C—N(CH₂CH₂Cl)—CH₂CH₂—O—CH(CH₃)₂ | 181.7 |
|  | (DP-8) H₃C—N(CH₂CH₂—O—CH(CH₃)₂)—CH₂CH₂—O—CH(CH₃)₂ | 206.35 |

TABLE 24-continued
| Nucleophile | Proposed Nitrogen Mustard Degradation Product | Calculated m/z value |
|---|---|---|
| 2-(2-ethoxy ethoxy)ethanol | <br>(DP-9) | 255.77 |
| | 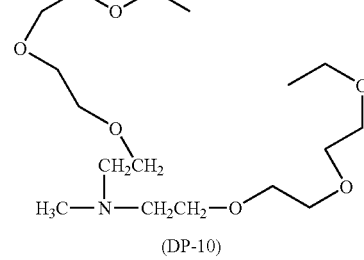<br>(DP-10) | 354.49 |
| Butylated hydroxytoluene | 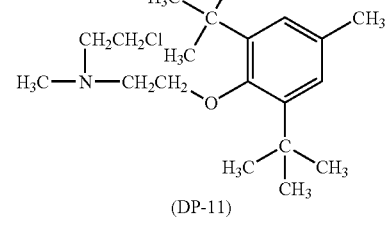<br>(DP-11) | 341.95 |
| | 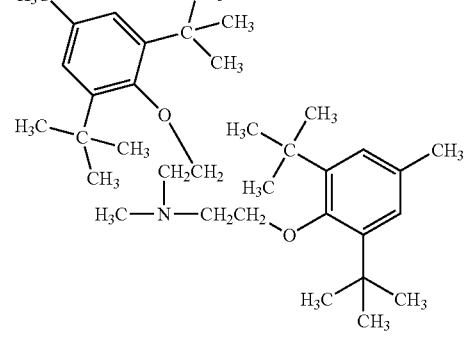<br>(DP-12) | 526.85 |
| Menthol | 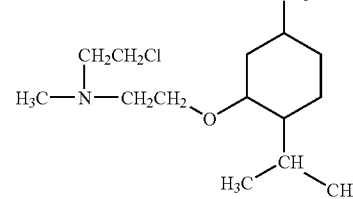<br>(DP-13) | 277.87 |

TABLE 24-continued

| Nucleophile | Proposed Nitrogen Mustard Degradation Product | Calculated m/z value |
|---|---|---|
|  | (DP-14) | 398.69 |
| Propylene glycol | (DP-15) | 196.1104 |
| Lactic acid | (DP-16) | 282.1128 |

Figure 10:
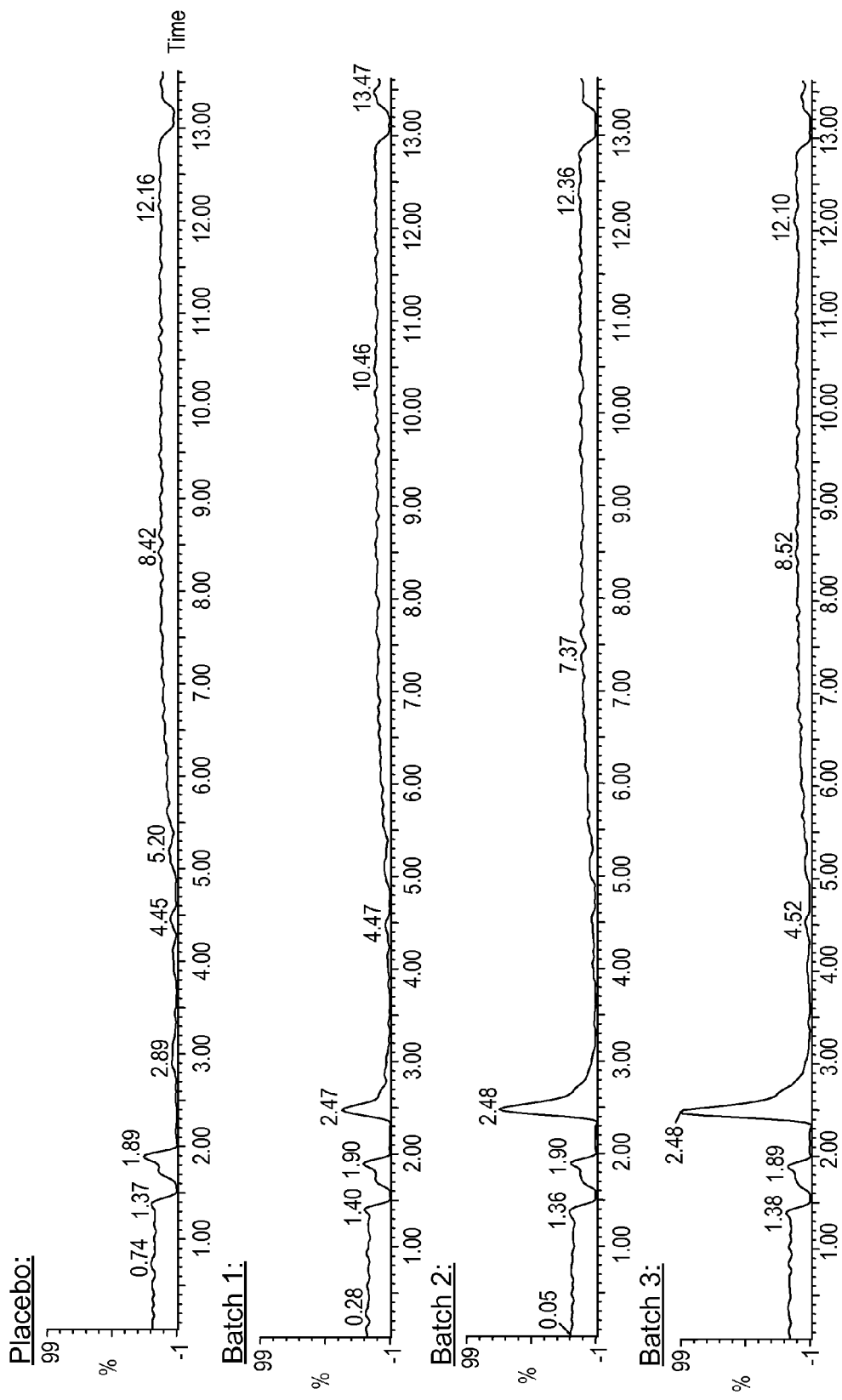
FIG. 10 depicts the results of mass spectrometry analysis measuring the presence and amount of (DP-15) in MCHCl 0.02% ointment batches stored at 2-8° C., as described in Example 11.
Figure 11:
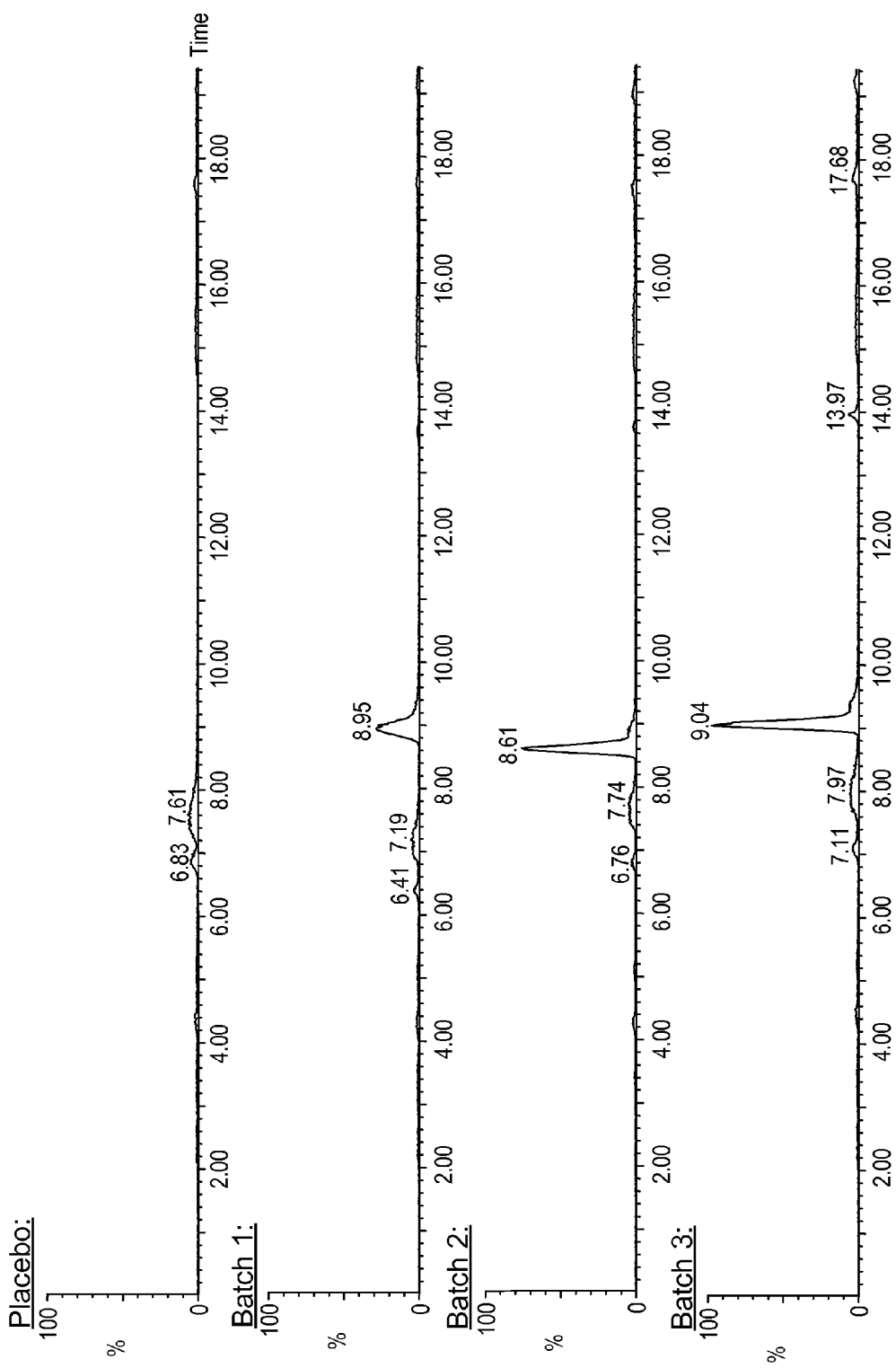
FIG. 11 depicts the results of mass spectrometry analysis measuring the presence and amount of (DP-16) in MCHCl 0.02% ointment batches stored at 2-8° C., as described in Example 11.

Surprisingly, none of degradation products (DP-1) to (DP-14) were detected in any of Batches 1, 2, or 3. Degradation products (DP-15) and (DP-16), however, were detected in all three batches, as illustrated by FIGS. 10 and 11, which represent the extracted ion currents for m/z 196 (i.e., (DP-15)) and 282 (i.e., (DP-16)), respectively.

Example 12

Effect of Temperature on Nitrogen Mustard Degradation Products

Four batches of ointment having 0.02% w/w mechlorethamine HCl were prepared according to Composition D above and stored for 24 hours at various temperatures. Batch 1 was stored at 2° C. to 8° C., Batch 2 was stored at 15° C. to 20° C., and Batch 3 was stored at 50° C. Batch 4 was stored at 15° C. to 20° C. and was spiked with 1% water. The presence of the nitrogen mustard degradation products in each batch was determined by LC-MS. The results are summarized in Table 25 below.

TABLE 25

| Degradation Product | Batch 1 (2° C. to 8° C.) | Batch 2 (15° C. to 20° C.) | Batch 3 (50° C.) | Batch 4 (15° C. to 20° C. + 1% water) |
|---|---|---|---|---|
| (DP-15) | 1% | 1% | 9% | 1% |
| (DP-16) | 0% | 0% | 10% | 0% |
| Half-mustard | 0% | 0% | 1% | 0% |
| Total degradation product | 1% | 1% | 20% | 1% |
| LCMS (assay) | 98% | 97% | 92% | 96% |

As illustrated by the data in Table 25, the amount of nitrogen mustard degradation product formed did not change significantly upon storage between 2° C. and 20° C., but increased when the storage temperature was raised to 50° C. Further, the addition of water did not affect the amount of nitrogen mustard degradation product formed.

The following are some illustrative embodiments of the invention:

1. A topical composition comprising: (a) an effective amount of an alkylating agent or a pharmaceutically acceptable salt or solvate thereof; and (b) a pharmaceutically acceptable excipient, wherein at least about 90% of the alkylating agent or pharmaceutically acceptable salt or solvate thereof is present in the composition after storage for at least about 3 months at a temperature of about −20° C. or higher.

2. The composition of embodiment 1, wherein at least about 90% of the alkylating agent or pharmaceutically acceptable salt or solvate thereof is present in the composition after storage for at least about 3 months at a temperature of about 2° C. or higher.

3. The composition of embodiment 1, wherein at least about 90% of the alkylating agent or pharmaceutically acceptable salt or solvate thereof is present in the composition after storage for at least about 3 months at a temperature of about 2° C. to about 8° C.

4. The composition of embodiment 1, wherein at least about 90% of the alkylating agent or pharmaceutically acceptable salt or solvate thereof is present in the composition after storage for at least about 6 months at a temperature of about 2° C. to about 8° C.

5. The composition of embodiment 1, wherein at least about 90% of the alkylating agent or pharmaceutically acceptable salt or solvate thereof is present in the composition after storage for at least about 12 months at a temperature of about 2° C. to about 8° C.

6. The composition of embodiment 1, wherein at least about 90% of the alkylating agent or pharmaceutically acceptable salt or solvate thereof is present in the composition after storage for at least about 24 months at a temperature of about 2° C. to about 8° C.

7. The composition of embodiment 1, wherein at least about 90% of the alkylating agent or pharmaceutically acceptable salt or solvate thereof is present in the composition after storage for at least about 3 months at a temperature of −20° C. to about −10° C.

8. The composition of embodiment 1, wherein at least about 90% of the bis-(2-chloroethyl)methylamine or pharmaceutically acceptable salt or solvate thereof is present in the composition after storage for at least about 6 months at a temperature of about −20° C. to about −10° C.

9. The composition of embodiment 1, wherein at least about 90% of the alkylating agent or pharmaceutically acceptable salt or solvate thereof is present in the composition after storage for at least about 12 months at a temperature of about −20° C. to about −10° C.

10. The composition of embodiment 1, wherein at least about 90% of the alkylating agent or pharmaceutically acceptable salt or solvate thereof is present in the composition after storage for at least about 24 months at a temperature of about −20° C. to about −10° C.

11. A topical composition comprising: (a) an effective amount of an alkylating agent or a pharmaceutically acceptable salt or solvate thereof; and (b) a pharmaceutically acceptable excipient, wherein at least about 90% of the alkylating agent or pharmaceutically acceptable salt or solvate thereof is present in the composition after storage for at least about 1 month at a temperature of about 15° C. to about 30° C.

12. The composition of embodiment 11, wherein at least about 90% of the alkylating agent or pharmaceutically acceptable salt or solvate thereof is present in the composition after storage for at least about 2 months at a temperature of about 15° C. to about 30° C.

13. The composition of embodiment 11, wherein at least about 90% of the alkylating agent or pharmaceutically acceptable salt or solvate thereof is present in the composition after storage for at least about 3 months at a temperature of about 15° C. to about 30° C.

14. The composition of embodiment 11, wherein at least about 90% of the alkylating agent or pharmaceutically acceptable salt or solvate thereof is present in the composition after storage for at least about 6 months at a temperature of about 15° C. to about 30° C.

15. The composition of embodiment 11, wherein at least about 90% of the alkylating agent or pharmaceutically acceptable salt or solvate thereof is present in the composition after storage for at least about 12 months at a temperature of about 15° C. to about 30° C.

16. The composition of embodiment 11, wherein at least about 90% of the alkylating agent or pharmaceutically acceptable salt or solvate thereof is present in the composition after storage for at least about 24 months at a temperature of about 15° C. to about 30° C.

17. The composition of any one of embodiments 1 to 16, wherein the alkylating agent is a nitrogen mustard.

18. The composition of embodiment 17, wherein the nitrogen mustard is a compound of the following Structure (VII), (VIII), (IX), (X), (XII), (XIII), (XIV), (XV), (XVI), (XVII), (XVIII), or (XIX):

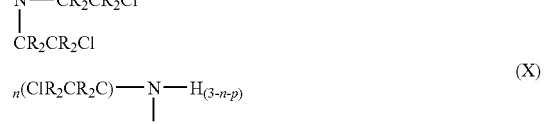
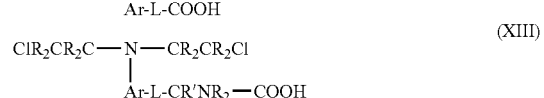

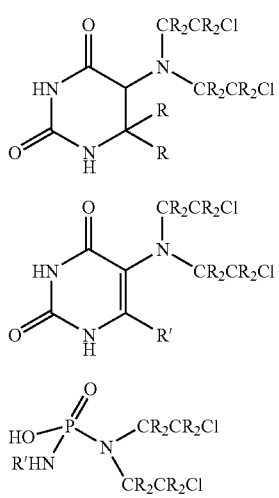

wherein:

each R and R' is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein any two R in the same molecule are optionally linked to form a three- to eight-membered cyclic group;

Z is a linear alkyl group having 1-6 carbon atoms;

each L is independently a linking group selected from the group consisting of linear or branched alkylene having 1 to 7 carbon atoms, cycloalkylene having 3 to 17 carbon atoms, alkylcycloalkylene having 4 to 20 carbon atoms, a cycloalkylalkylene having 4 to 20 carbon atoms, an arylene, having 4 to 30 carbon atoms, an alkylarylene, having 4 to 30 carbon atoms, an arylalkylene, having 4 to 30 carbon atoms, and combinations thereof;

each Ar is independently a bifunctional aromatic linking group wherein each Ar is selected from the group consisting of arylene, substituted arylene and heteroarylene;

n is 1, 2, or 3;

p is 0, 1, or 2; and

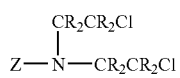

19. The composition of embodiment 17, wherein the nitrogen mustard is a compound of the following Structure (XVII)

(XVII)

Z—N—CR$_2$CR$_2$Cl
     |
     CR$_2$CR$_2$Cl wherein Z is a linear alkyl group having 1-6 carbon atoms and each R is independently hydrogen or a linear alkyl group having 1-6 carbon atoms.

20. The composition of embodiment 19, wherein Z is methyl or ethyl.

21. The composition of embodiment 17, wherein the nitrogen mustard is bis-(2-chloroethyl)ethylamine, bis-(2-chloroethyl)methylamine, or tris-(2-chloroethyl)amine.

22. The composition of any one of embodiments 1 to 21, wherein the nitrogen mustard is bis-(2-chloroethyl)methylamine.

23. The composition of any one of embodiments 1 to 22, wherein the composition has a viscosity of about 5,000 cps to about 50,000 cps.

24. The composition of any one of embodiments 1 to 22, wherein the composition has a viscosity of about 15,000 cps to about 40,000 cps.

25. The composition of any one of embodiments 1 to 22, wherein the composition has a viscosity of about 20,000 cps to about 35,000 cps.

26. A method for treating a skin disorder comprising topically applying to a subject in need thereof a composition of any one of embodiments 1 to 25.

27. The method of embodiment 26, wherein the skin disorder is psoriasis, eczema, actinic keratosis, lupus, sarcoidosis, alopecia, cutaneous T-Cell lymphoma, mycosis fungoides, lymphoreticular neoplasia, pleural or peritoneal effusions, cutaneous B-cell lymphoma, pseudolymphoma of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease, or vitiligo.

28. The method of embodiment 26, wherein the skin disorder is a T-cell mediated skin disorder.

29. The method of embodiment 28, wherein the T-cell mediated skin disorder is psoriasis, actinic keratosis, cutaneous T-cell lymphoma, cutaneous B-cell lymphoma, mycosis fungoides, alopecia, alopecia areata, or vitiligo.

30. The method of embodiment 26, wherein the skin disorder is mycosis fungoides.

31. A topical composition comprising: (a) an effective amount of a nitrogen mustard or a pharmaceutically acceptable salt or solvate thereof; and (b) a pharmaceutically acceptable excipient, wherein the composition contains less than about 10% by weight of nitrogen mustard degradation product after storage for at least about 3 months at a temperature of about −20° C. or higher.

32. The composition of embodiment 31, wherein the composition contains less than about 10% by weight of the nitrogen mustard degradation product after storage for at least about 3 months at a temperature of about 2° C. or higher.

33. The composition of embodiment 31, wherein the composition contains less than about 10% by weight of the nitrogen mustard degradation product after storage for at least about 3 months at a temperature of about 2° C. to about 8° C.

34. The composition of embodiment 31, wherein the composition contains less than about 10% by weight of the nitrogen mustard degradation product after storage for at least about 6 months at a temperature of about 2° C. to about 8° C.

35. The composition of embodiment 31, wherein the composition contains less than about 10% by weight of the nitrogen mustard degradation product after storage for at least about 12 months at a temperature of about 2° C. to about 8° C.

36. The composition of embodiment 31, wherein the composition contains less than about 10% by weight of the nitrogen mustard degradation product after storage for at least about 24 months at a temperature of about 2° C. to about 8° C.

37. The composition of embodiment 31, wherein the composition contains less than about 10% by weight of the nitrogen mustard degradation product after storage for at least about 3 months at a temperature of about −20° C. to about −10° C.

38. The composition of embodiment 31, wherein the composition contains less than about 10% by weight of the nitrogen mustard degradation product after storage for at least about 6 months at a temperature of about −20° C. to about −10° C.

39. The composition of embodiment 31, wherein the composition contains less than about 10% by weight of the nitrogen mustard degradation product after storage for at least about 12 months at a temperature of about −20° C. to about −10° C.

40. The composition of embodiment 31, wherein the composition contains less than about 10% by weight of the nitrogen mustard degradation product after storage for at least about 24 months at a temperature of about −20° C. to about −10° C.

41. A topical composition comprising: (a) an effective amount of a nitrogen mustard or a pharmaceutically acceptable salt or solvate thereof; and (b) a pharmaceutically acceptable excipient, wherein the composition contains less than about 10% by weight of nitrogen mustard degradation product after storage for at least about 1 month at a temperature of about 15° C. to about 30° C.

42. The composition of embodiment 41, wherein the composition contains less than about 10% by weight of the nitrogen mustard degradation product after storage for at least about 2 months at a temperature of about 15° C. to about 30° C.

43. The composition of embodiment 41, wherein the composition contains less than about 10% by weight of the nitrogen mustard degradation product after storage for at least about 3 months at a temperature of about 15° C. to about 30° C.

44. The composition of embodiment 41, wherein the composition contains less than about 10% by weight of the nitrogen mustard degradation product after storage for at least about 6 months at a temperature of about 15° C. to about 30° C.

45. The composition of embodiment 41, wherein the composition contains less than about 10% by weight of the nitrogen mustard degradation product after storage for at least about 12 months at a temperature of about 15° C. to about 30° C.

46. The composition of embodiment 41, wherein the composition contains less than about 10% by weight of the nitrogen mustard degradation product after storage for at least about 24 months at a temperature of about 15° C. to about 30° C.

47. The composition of any one of embodiments 31 to 46, wherein the nitrogen mustard degradation product is a half-mustard.

48. The composition of any one of embodiments 31 to 47, wherein the nitrogen mustard is a compound of the following Structure (VII), (VIII), (IX), (X), (XII), (XIII), (XIV), (XV), (XVI), (XVII), (XVIII), or (XIX):

(VII)

(XV)

(XVI)

(XVII)

(VIII)

(IX)

(X)

(XII)

(XIII)

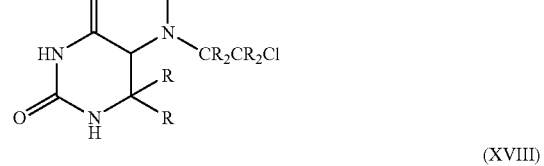

(XIV)

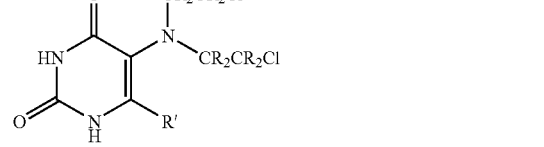

(XVIII)

(XIX)

wherein:
each R and R' is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, and an alkynylacyl group, wherein any two R in the same molecule are optionally linked to form a three- to eight-membered cyclic group;

Z is a linear alkyl group having 1-6 carbon atoms;

each L is independently a linking group selected from the group consisting of linear or branched alkylene having 1 to 7 carbon atoms, cycloalkylene having 3 to 17 carbon atoms, alkylcycloalkylene having 4 to 20 carbon atoms, a cycloalkylalkylene having 4 to 20 carbon atoms, an arylene, having 4 to 30 carbon atoms, an alkylarylene, having 4 to 30 carbon atoms, an arylalkylene, having 4 to 30 carbon atoms, and combinations thereof;

each Ar is independently a bifunctional aromatic linking group wherein each Ar is selected from the group consisting of arylene, substituted arylene and heteroarylene;

n is 1, 2, or 3;

p is 0, 1, or 2; and $n+p \leq 3$.

49. The composition of any one of embodiments 31 to 46, wherein the nitrogen mustard is a compound of the following Structure (XVII)

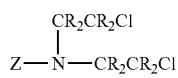
(XVII)

wherein Z is a linear alkyl group having 1-6 carbon atoms and each R is independently hydrogen or a linear alkyl group having 1-6 carbon atoms.

50. The composition of embodiment 49, wherein the nitrogen mustard degradation product has the following structure (DP-A) or (DP-C):

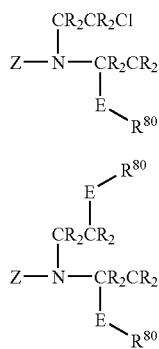

wherein:

Z is a linear alkyl group having 1-6 carbon atoms;

each R is independently hydrogen or a linear alkyl group having 1-6 carbon atoms;

each E is independently —O—, —NH—, —S—; —OC(O)CH($CH_3$)OC(O)CH($CH_3$)—; —OCH($CH_3$)C(O)OCH($CH_3$)—; or —O($CH_2$)$_2$O($CH_2$)$_2$O—; and each $R^{80}$ is independently a linear or branched alkyl group having 1-12 carbon atoms, —COOH, or —OH.

51. The composition of any one of embodiments 31 to 46, wherein the nitrogen mustard is bis-(2-chloroethyl)ethylamine, bis-(2-chloroethyl)methylamine, or tris-(2-chloroethyl)amine.

52. The composition of any one of embodiments 31 to 46, wherein the nitrogen mustard is bis-(2-chloroethyl)methylamine.

53. The composition of embodiment 52, wherein the nitrogen mustard degradation product has the following structure (DP-B) or (DP-D):

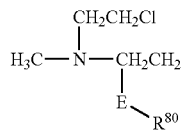
(DP-B)

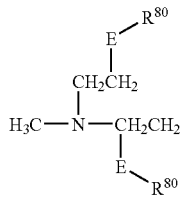
(DP-D)

wherein:

each E is independently —O—, —NH—, —S—; —OC(O)CH($CH_3$)OC(O)CH($CH_3$)—; —OCH($CH_3$)C(O)OCH($CH_3$)—; or —O($CH_2$)$_2$O($CH_2$)$_2$O—; and each $R^{80}$ is independently a linear or branched alkyl group having 1-12 carbon atoms, —COOH, or —OH.

54. The composition of embodiment 53, wherein the nitrogen mustard degradation product is

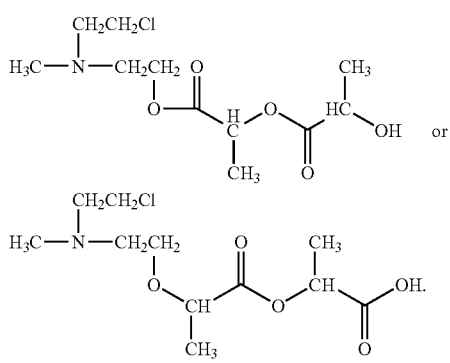

55. The composition of embodiment 53, wherein the nitrogen mustard degradation product is

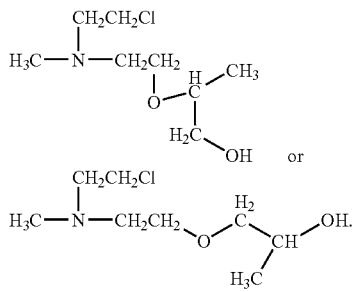

56. The composition of embodiment 53, wherein the nitrogen mustard degradation product is

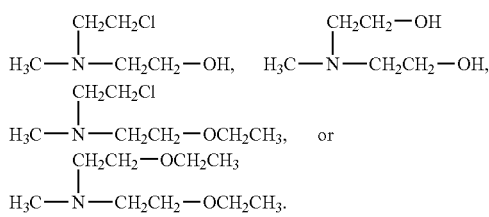

57. The composition of any one of embodiments 31 to 57, wherein the composition has a viscosity of about 5,000 cps to about 50,000 cps.

58. The composition of any one of embodiments 31 to 57, wherein the composition has a viscosity of about 15,000 cps to about 40,000 cps.

59. The composition of any one of embodiments 31 to 57, wherein the composition has a viscosity of about 20,000 cps to about 35,000 cps.

60. A method for treating a skin disorder comprising topically applying to a subject in need thereof a composition of any one of embodiments 31 to 57.

61. The method of embodiment 60, wherein the skin disorder is psoriasis, eczema, actinic keratosis, lupus, sarcoidosis, alopecia, cutaneous T-Cell lymphoma, mycosis fungoides, lymphoreticular neoplasia, pleural or peritoneal effusions, cutaneous B-cell lymphoma, pseudolymphoma of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease, or vitiligo.

62. The method of embodiment 60, wherein the skin disorder is a T-cell mediated skin disorder.

63. The method of embodiment 62, wherein the T-cell mediated skin disorder is psoriasis, actinic keratosis, cutaneous T-cell lymphoma, cutaneous B-cell lymphoma, mycosis fungoides, alopecia, alopecia areata, or vitiligo.

64. The method of embodiment 60, wherein the skin disorder is mycosis fungoides.

65. The composition of any one of embodiments 1 to 25 or 31 to 59, wherein the pharmaceutically acceptable excipient is a diethylene glycol monosubstituted ether.

66. The composition of any one of embodiments 1 to 25 or 31 to 59, wherein the pharmaceutically acceptable excipient is a compound of the formula $HOCH_2CH_2OCH_2CH_2OR_{79}$, wherein $R_{79}$ is a linear alkyl group having 1-6 carbon atoms.

67. The composition of any one of embodiments 1 to 25 or 31 to 59, wherein the pharmaceutically acceptable excipient is 2-(2-ethoxyethoxy)ethanol.

68. The composition of any one of embodiments 1 to 25 or 31 to 59, wherein the pharmaceutically acceptable excipient is a polyoxylglyceride.

69. The composition of any one of embodiments 1 to 25, 31 to 59 or 65 to 68, wherein the pharmaceutically acceptable excipient is an antioxidant.

70. The composition of embodiment 69, wherein the antioxidant is butylated hydroxytoluene, edetate disodium, benzyl alcohol, ascorbic acid, citric acid, malic acid, fumaric acid, lactic acid, or propionic acid.

71. The composition of embodiment 69, wherein the antioxidant is butylated hydroxytoluene or edetate disodium.

72. The composition of any one of embodiments 1 to 25, 31 to 59, or 65 to 71, wherein the pharmaceutically acceptable excipient is an organic acid.

73. A topical composition comprising: (a) an effective amount of bis-(2-chloroethyl) methylamine or a pharmaceutically acceptable salt or solvate thereof; and (b) a nitrogen mustard degradation product of the following Structure (DP-B) or (DP-D)

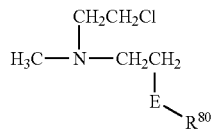
(DP-B)

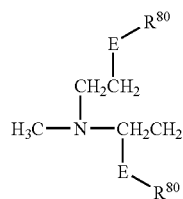
(DP-D)

wherein:
each E is independently —O—, —NH—, —S—; —OC(O)CH($CH_3$)OC(O)CH($CH_3$)—; —OCH($CH_3$)C(O)OCH($CH_3$)—; or —O($CH_2$)$_2$O($CH_2$)$_2$O—; and
each $R^{80}$ is independently a linear or branched alkyl group having 1-12 carbon atoms, —COOH, or —OH.

74. The composition of embodiment 73, wherein the nitrogen mustard degradation product is:

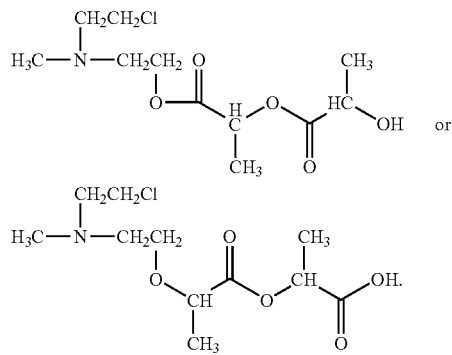

75. The composition of embodiment 73, wherein the nitrogen mustard degradation product is:

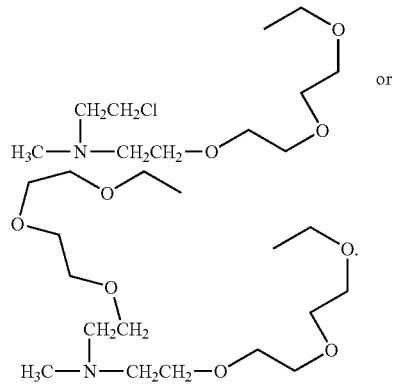

76. A method for treating a skin disorder comprising topically applying to a subject in need thereof a composition of any one of embodiments 73 to 75.

77. The method of embodiment 76, wherein the skin disorder is psoriasis, eczema, actinic keratosis, lupus, sarcoidosis, alopecia, cutaneous T-Cell lymphoma, mycosis fungoides, lymphoreticular neoplasia, pleural or peritoneal effusions, cutaneous B-cell lymphoma, pseudolymphoma of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease, or vitiligo.

78. The method of embodiment 76, wherein the skin disorder is a T-cell mediated skin disorder.

79. The method of embodiment 78, wherein the T-cell mediated skin disorder is psoriasis, actinic keratosis, cutaneous T-cell lymphoma, cutaneous B-cell lymphoma, mycosis fungoides, alopecia, alopecia areata, or vitiligo.

80. The method of embodiment 76, wherein the skin disorder is mycosis fungoides.

We claim:

1. A topical composition comprising: (a) an effective amount of bis-(2-chloroethyl)methylamine or a pharmaceutically acceptable salt or solvate thereof; and (b) a pharmaceutically acceptable excipient comprising a compound of the formula $HOCH_2CH_2OCH_2CH_2OR_{79}$, wherein $R_{79}$ is a linear alkyl group having 1-6 carbon atoms, wherein at least about 90% of the bis-(2-chloroethyl)methylamine or pharmaceutically acceptable salt or solvate thereof is present in the composition after storage for at least about 3 months to about 3 years at a temperature of about −20° C. to about 8° C.

2. The composition of claim 1, wherein at least about 90% of the bis-(2-chloroethyl)methylamine or pharmaceutically acceptable salt or solvate thereof is present in the composition after storage for at least about 3 months to about 3 years at a temperature of about 2° C. to about 8° C.

3. The composition of claim 1, wherein at least about 90% of the bis-(2-chloroethyl)methylamine or pharmaceutically acceptable salt or solvate thereof is present in the composition after storage for at least about 6 months to about 3 years at a temperature of about 2° C. to about 8° C.

4. The composition of claim 1, wherein at least about 90% of the bis-(2-chloroethyl)methylamine or pharmaceutically acceptable salt or solvate thereof is present in the composition after storage for at least about 12 months to about 3 years at a temperature of about 2° C. to about 8° C.

5. The composition of claim 1, wherein at least about 90% of the bis-(2-chloroethyl)methylamine or pharmaceutically acceptable salt or solvate thereof is present in the composition after storage for at least about 24 months to about 3 years at a temperature of about 2° C. to about 8° C.

6. The composition of claim 1, wherein at least about 90% of the bis-(2-chloroethyl)methylamine or pharmaceutically acceptable salt or solvate thereof is present in the composition after storage for at least about 3 months to about 3 years at a temperature of about −20° C. to about −10° C.

7. The composition of claim 1, wherein at least about 90% of the bis-(2-chloroethyl)methylamine or pharmaceutically acceptable salt or solvate thereof is present in the composition after storage for at least about 6 months to about 3 years at a temperature of about −20° C. to about −10° C.

8. The composition of claim 1, wherein at least about 90% of the bis-(2-chloroethyl)methylamine or pharmaceutically acceptable salt or solvate thereof is present in the composition after storage for at least about 12 months to about 3 years at a temperature of about −20° C. to about −10° C.

9. The composition of claim 1, wherein at least about 90% of the bis-(2-chloroethyl)methylamine or pharmaceutically acceptable salt or solvate thereof is present in the composition after storage for at least about 24 months to about 3 years at a temperature of about −20° C. to about −10° C.

10. A topical composition comprising: (a) an effective amount of bis-(2-chloroethyl)methylamine or a pharmaceutically acceptable salt or solvate thereof; and (b) a pharmaceutically acceptable excipient comprising a compound of the formula $HOCH_2CH_2OCH_2CH_2OR_{79}$, wherein $R_{79}$ is a linear alkyl group having 1-6 carbon atoms, wherein the composition contains less than about 10% by weight of nitrogen mustard degradation product after storage for about 3 months to about 3 years at a temperature of about −20° C. to about 8° C.

11. The composition of claim 10, wherein the nitrogen mustard degradation product is a half-mustard.

12. The composition of claim 11, wherein the half-mustard has the following structure (DP-B):

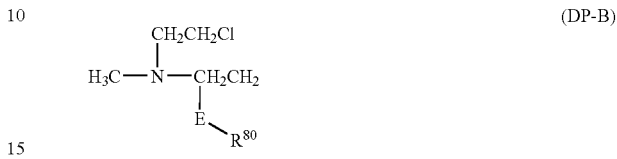

wherein:
E is —O—, —NH—, —S—; —OC(O)CH($CH_3$)OC(O)CH($CH_3$)-; —OCH($CH_3$)C(O)OCH($CH_3$)-; or —O($CH_2$)$_{20}$($CH_2$)$_{20}$-; and
$R^{80}$ is a linear or branched alkyl group having 1-12 carbon atoms, —COOH, or —OH.

13. The composition of claim 10, wherein the nitrogen mustard degradation product is

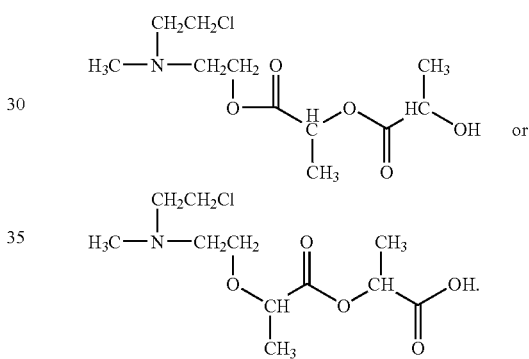

14. The composition of claim 10, wherein the nitrogen mustard degradation product is

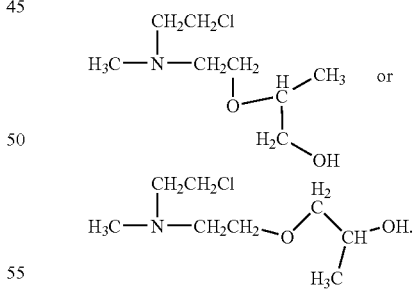

15. The composition of claim 10, wherein the nitrogen mustard degradation product is

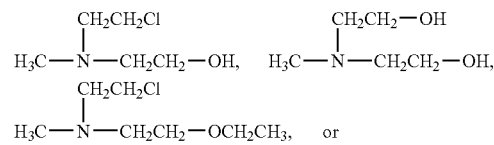

-continued

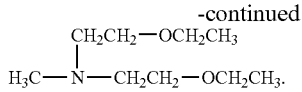

16. The composition of claim 10, wherein the composition contains less than about 10% by weight of the nitrogen mustard degradation product after storage for at least about 3 months to about 3 years at a temperature of about 2° C. to about 8° C.

17. The composition of claim 10, wherein the composition contains less than about 10% by weight of the nitrogen mustard degradation product after storage for at least about 6 months to about 3 years at a temperature of about 2° C. to about 8° C.

18. The composition of claim 10, wherein the composition contains less than about 10% by weight of the nitrogen mustard degradation product after storage for at least about 12 months to about 3 years at a temperature of about 2° C. to about 8° C.

19. The composition of claim 10, wherein the composition contains less than about 10% by weight of the nitrogen mustard degradation product after storage for at least about 24 months to about 3 years at a temperature of about 2° C. to about 8° C.

20. The composition of claim 10, wherein the composition contains less than about 10% by weight of the nitrogen mustard degradation product after storage for at least about 3 months to about 3 years at a temperature of about −20° C. to about −10° C.

21. The composition of claim 10, wherein the composition contains less than about 10% by weight of the nitrogen mustard degradation product after storage for at least about 6 months to about 3 years at a temperature of about −20° C. to about −10° C.

22. The composition of claim 10, wherein the composition contains less than about 10% by weight of the nitrogen mustard degradation product after storage for at least about 12 months to about 3 years at a temperature of about −20° C. to about −10° C.

23. The composition of claim 10, wherein the composition contains less than about 10% by weight of the nitrogen mustard degradation product after storage for at least about 24 months to about 3 years at a temperature of about −20° C. to about −10° C.

24. The composition of claim 10, wherein the nitrogen mustard degradation product is:

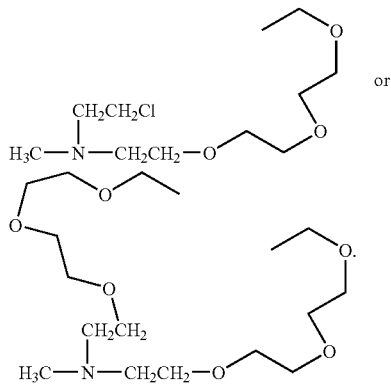

* * * * *

UNITED STATES PATENT AND TRADEMARK OFFICE
CERTIFICATE OF CORRECTION

| | | |
|---|---|---|
| PATENT NO. | : 8,501,818 B2 | Page 1 of 1 |
| APPLICATION NO. | : 12/687605 | |
| DATED | : August 6, 2013 | |
| INVENTOR(S) | : Alonso et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 153 days.

Signed and Sealed this
Seventh Day of April, 2015

Michelle K. Lee
*Director of the United States Patent and Trademark Office*